United States Patent
Kobayashi et al.

(10) Patent No.: US 10,865,429 B2
(45) Date of Patent: Dec. 15, 2020

(54) MICROORGANISM HAVING PHA SYNTHASE-CODING GENES AND METHOD FOR PRODUCING PHA USING SAME

(71) Applicant: KANEKA CORPORATION, Osaka (JP)

(72) Inventors: Shingo Kobayashi, Takasago (JP); Hitoshi Sashiwa, Settsu (JP); Tetsuya Fujiki, Takasago (JP)

(73) Assignee: KANEKA CORPORATION, Osaka (JP)

( * ) Notice: Subject to any disclaimer, the term of this patent is extended or adjusted under 35 U.S.C. 154(b) by 232 days.

(21) Appl. No.: 15/763,323

(22) PCT Filed: Sep. 15, 2016

(86) PCT No.: PCT/JP2016/004222
§ 371 (c)(1),
(2) Date: Mar. 26, 2018

(87) PCT Pub. No.: WO2017/056442
PCT Pub. Date: Apr. 6, 2017

(65) Prior Publication Data
US 2018/0305722 A1 Oct. 25, 2018

(30) Foreign Application Priority Data
Sep. 28, 2015 (JP) .................. 2015-190269

(51) Int. Cl.
| | | |
|---|---|---|
| C12N 1/20 | (2006.01) | |
| C12N 15/74 | (2006.01) | |
| C12P 7/62 | (2006.01) | |
| C12N 9/10 | (2006.01) | |
| C08G 63/06 | (2006.01) | |

(52) U.S. Cl.
CPC ............. *C12P 7/625* (2013.01); *C08G 63/06* (2013.01); *C12N 1/20* (2013.01); *C12N 9/1029* (2013.01); *C12N 15/74* (2013.01); *C12Y 203/01* (2013.01)

(58) Field of Classification Search
None
See application file for complete search history.

(56) References Cited

U.S. PATENT DOCUMENTS

2014/0088288 A1 3/2014 Iwata
2018/0305722 A1* 10/2018 Kobayashi ............ C08G 63/06

FOREIGN PATENT DOCUMENTS

| JP | 6-157878 A | 6/1994 |
| JP | 8-510498 A | 11/1996 |
| JP | 2004-250629 A | 9/2004 |
| JP | 2015-29484 A | 2/2015 |
| WO | WO 94/28070 A1 | 12/1994 |
| WO | WO 02/50156 A2 | 6/2002 |
| WO | WO 02/50156 A3 | 6/2002 |
| WO | WO 2012/133231 A1 | 10/2012 |
| WO | WO 2015/133468 A1 | 9/2015 |
| WO | WO 2015/146195 A1 | 10/2015 |

OTHER PUBLICATIONS

International Search Report dated Dec. 6, 2016, in PCT/JP2018/004222 filed Sep. 15, 2013.

Lu, X., "Molecular Cloning and Functional Analysis of Two Polyhydroxyalkanoate Synthases from Two Strains of *Aeromonas hydrophila* Spp.", FEMS Microbiology Letters, vol. 243, No. 1, (2005), pp. 149-155.

Tsuge, T. et al., "Combination of N149S and D171G Mutations in Aeromonas Caviae Polyhydroxyalkanoate Synthase and Impact on Polyhydroxyalkanoate Biosynthesis", FEMS Microbiological Research Leetter, vol. 277, No. 2, (2007), pp. 217-222.

Tsuge, T. et al., "Variation in Copolymer Composition and Molecular Weight of Polyhydroxyalkanoate Generated by Saturation Mutagenesis of Aeromonas Caviae PHA Synthase", Macromolecular Bioscience, vol. 7, No. 6, (2007), (11 total pages).

Lee, W-H et al., "Biosynthesis of Polyhydroxyalkanoate Copolymers from Mixtures of Plant Oils and 3-Hydroxyvalerate Precursors", ScienceDirect, Bioresource Technology, vol. 99, (2008), pp. 6844-6851.

Matsusaki, H. et al., "Cloning and Molecular Analysis of the Poly(3-hydroxybutyrate) and Poly(3-hydroxybutyrate-co-3-hydroxyalkanoate) Biosynthesis Genes in *Pseudomonas* sp. Strain 61-3", Journal of Bacteriology, vol. 180, No. 24, (1998), pp. 6459-6467.

Timm, A. et al., "Formation of Blends of Various Poly(3-Hydroxyalkanoic Acids) by a Recombinant Strain of *Pseudomonas oleovorans*", Applied Mocrobiology and Biotechnology, vol. 33, (1990), pp. 296-301.

(Continued)

*Primary Examiner* — Padmavathi Baskar
(74) *Attorney, Agent, or Firm* — Oblon, McClelland, Maier & Neustadt, L.L.P.

(57) ABSTRACT

An object of the invention is to improve the crystallization speed of a PHA copolymer which is to be slowly crystallized, and improve the melt workability and productivity. A microorganism is used which has genes encoding two or more different PHA synthases derived from the genus *Aeromonas*. The genes encoding the PHA synthases derived from the genus *Aeromonas* preferably include genes encoding at least two PHA synthases which are capable of synthesizing a copolymer PHA including, as monomer unit species, 3-hydroxybutyric acid and 3-hydroxyhexanoic acid, and which are different in substrate specificity toward 3-hydroxyhexanoic acid from each other. When this microorganism is cultured, a PHA mixture can be produced which includes three or more PHA species different in melting point from each other.

12 Claims, No Drawings
Specification includes a Sequence Listing.

(56) References Cited

OTHER PUBLICATIONS

Liebergesell, M. et al., "Analysis of Polyhydroxyalkanoic Acid-Biosynthesis Genes of Anoxygenic Phototrophic Bacteria Reveals Synthesis of a Polyester Exhibiting an Unusual Composition", Applied Microbiology and Biotechnology, vol. 40, (1993), pp. 292-300.
Aneja, K. et al., "Altered composition of Ralstonla Eutropha Poly (hydroxyalkanoate) Through Expression of PHA Synthase from Allochromatium Vinosum ATCC 35206", Biotechnol Lett. vol. 31, (2009), pp. 1601-1612.
Extended European Search Report dated May 9, 2019 in Patent Application No. 16850623.6, 7 pages.
Jin Han, et al., "Engineered Aeromonas Hydrophila for Enhanced Production of Poly(3-Hydroxybutyrate-co-3-Hydroxyhexanoate) with Alterable Monomers Composition" FEMS Microbiology Letters, vol. 239. No. 1, XP004579971, Oct. 1, 2004, pp. 195-201.

* cited by examiner

MICROORGANISM HAVING PHA SYNTHASE-CODING GENES AND METHOD FOR PRODUCING PHA USING SAME

TECHNICAL FIELD

The present invention relates to a microorganism for producing, in a cell thereof, PHAs; and a method for producing PHAs using the microorganism.

BACKGROUND ART

A polyhydroxyalkanoic acid (polyhydroxyalkanoate, abbreviated hereinafter to a "PHA") is a thermoplastic polyester produced and stored as an energy storing substance inside cells of many microorganism species. The PHA, which is produced from various natural carbon sources by microorganisms, is completely biodegraded by a microorganism in the earth or in water to be taken into a carbon cycle process in the natural world. It can be therefore stated that the PHA is an environment-harmonized type plastic material, which hardly produces any bad effect on the ecological system. In recent years, from the viewpoint of environmental pollution, waste disposal, and petroleum resources, synthetic plastics have been becoming a serious social problem. Thus, attention has been paid to PHAs as environment-friendly green plastic materials. It has been strongly desired to put PHAs into practical use.

A PHA discovered initially in microorganisms is a polyhydroxybutyric acid (poly-3-hydroxybutyrate, abbreviated hereinafter to a "PHB"), which is a homopolymer made from 3-hydroxybutyric acid (3-hydroxybutyrate, abbreviated hereinafter to "3HB"). The PHB is high in crystallinity, and is high in crystallization degree to be hard and brittle, and further the PHB is rapidly thermally decomposed at a temperature (180° C.) around the melting point thereof. Accordingly, the PHB has problems that this is low in melt workability and a practical use scope thereof is very restrictive.

Thus, in order to lower the PHB in crystallization degree to be improved in brittleness, attempts have been made in which another 3-hydroxyalkanoic acid is introduced into the skeleton of the PHB. In one of the attempts, a copolymer polyester has been discovered which is made from 3HB, and 3-hydroxyhexanoic acid (3-hydroxyhexanoate, abbreviated hereinafter to "3HH") (this polyester poly(3HB-co-3HH) will be abbreviated hereinafter to the "PHBH"). The PHBH, which contains as its monomer unit species 3HH having a longer side chain structure than 3HB, is lower in crystallization degree than any PHB to have flexible and soft properties and be improved in brittleness. Additionally, the PHBH is low in melting point to be also expected to have improved melt workability. However, the following have been understood: the PHBH is very low in crystallization/solidification speed; thus, even when cooled to room temperature after heated and melted, the PHBH is soft and viscous for some time; and the PHBH has adhesiveness so that when molded, the PHBH is not immediately released from the mold. For the reason, in the case of putting the PHBH into practical use, there is caused a problem that it is difficult to work the PHBH continuously. It has also become evident that working machines used to work existing commodity plastics high in crystallization/solidification speed may not be usable for working the PHBH. In working into a film or sheet, a fiber, a foam, a molded product, or a nonwoven fabric, it is very important when a melt-worked polymer is cooled that the crystallization/solidification speed of this polymer is high since this high speed results in making the producing process of such articles continuous, followed by an improvement of the articles in productivity and a fall in costs thereof.

Thus, attempts have been made for making a PHBH high in crystallization/solidification speed. As an ordinary method therefor, a method of adding, to the PHBH, a nucleating agent has been attempted. According to, for example, Patent Literature 1, boron nitride is used as the nucleating agent for PHBH to produce a crystallization promoting effect. However, this is an expensive material, and further has no biodegradability. Consequently, a less expensive and more biodegradable nucleating agent has been investigated.

Patent Literatures 2 and 3 each disclose a technique of adding a PHB, which is higher in melting point than a PHBH and is further biodegradable, as a nucleating agent to the PHBH to make the resultant high in crystallization/solidification speed. According to these preceding literatures, as a method of blending the PHBH with the PHB, for example, the following has been attempted: a method of dissolving the PHBH and the PHB in a solvent such as hot chloroform, blending these solutions with each other, and then evaporating chloroform to precipitate polymers; a method of pulverizing the two polymers to be blended with each other while the polymers are cooled with dry ice; or blending these polymers in the state that only the PHBH is melted without melting the PHB, or blending these polymers by mixing dry powders of the polymers with each other. However, the method of dissolving the polymers in the solvent to be mixed with each other requires a very large quantity of the solvent for dissolving or crystallizing the PHBH, so as to become high in costs. As the method of blending the PHBH with the PHB, a method is also known in which these polymers are subjected to crystallization with methanol and the resultant mixed polymers are collected. Because of a difference in solubility between the polymer and the nucleating agent at the time of the crystallization, this method has, for example, a probability that the crystallization may not be performed in the state that the nucleating agent is uniformly dispersed. Thus, this method is not practical. In the method of pulverizing the polymers and subsequently blending the polymers with each other, or the method of mixing the dry polymer powders, it is difficult to blend the polymers uniformly with each other. It is therefore anticipated that the effect of the nucleating agent is lowered. As the respective particle diameters of the PHBH and the nucleating agent are smaller, these are more sufficiently blended with each other and further the number of nucleus-forming moieties becomes larger. Thus, a higher advantageous effect is expected. However, in the blending methods described above, the blending effect based on such fine particles is not expectable. Furthermore, in order to disperse the PHB uniformly in the PHBH, working at a temperature not lower than the melting point of the PHB is required. However, ordinary species of the PHB have a high melting point. Additionally, as described above, the species are thermally decomposed at a temperature around the melting point. Thus, when the PHB is dispersed in the PHBH, the PHB and the PHBH are deteriorated by heat, so that a fall in the molecular weight thereof, and other problems are not easily avoidable.

In order to solve these problems, a method has been invented in which a microorganism is caused to produce a PHBH, and a PHA, which is a nucleating agent, in a mixed state by controlling the culture of the microorganism. For example, Patent Literature 4 reports a method of changing a carbon source in the middle of the culture to cause a microorganism to produce a mixture of a PHBH, and a PHB or another PHBH having a low copolymerization proportion of a 3HH monomer. Non-Patent Literature 1 suggests that a culture of a microorganism, using a specific plant oil and sodium valerate as carbon sources, makes it possible to co-produce, in a cell of the microorganism, a mixture of a PHB, and a copolymer polyester made from 3HB, and 3-hydroxyvaleric acid (3-hydroxyvalerate, abbreviated hereinafter to "3HV") (this polyester poly(3HB-co-3HV) will be abbreviated hereinafter to the "PHBV"). These methods do not require separate production of a nucleating agent component such as a PHB to have a large advantage in terms of costs. However, in the method in Patent Literature 4, in which a carbon source is changed in the middle of the culture, two PHAs are non-continuously produced so that the control of the culture is very difficult. Furthermore, the method is low in productivity so that the polymers are not stably produced with ease. Moreover, in the method in Non-Patent Literature 1, a target advantageous effect is obtained only when the specific plant oil is used. Furthermore, it is difficult to control a blend quantity ratio between the two PHAs. Thus, this method is impractical.

Additionally, as an example in which two PHAs are intracellularly co-produced, the following are reported: For example, Non-Patent Literature 2 reports that a wild type 61-3 strain of the genus *Pseudomonas* has genes encoding three PHA synthases. Two of these three PHA synthases have, as their substrate, a 3-hydroxyalkanoic acid having a carbon chain length of 6 to 12 (abbreviated hereinafter to a "medium-chain-length hydroxyalkanoic acid"), and one thereof has, as its substrate, only 3HB. Therefore, when this 61-3 strain is cultured in a culture medium containing a fatty acid such as octanoic acid or dodecanoic acid, a PHA made mainly of a medium-chain-length hydroxyalkanoic acid (abbreviated hereinafter to a "medium-chain-length PHA"), and a PHB are intracellularly co-produced. Non-Patent Literatures 3 and 4 each report that when a gene encoding a PHB synthase derived from a bacterium that may be of various types is introduced into a *Pseudomonas oleovorans*, which synthesizes a medium-chain-length PHA, the medium-chain-length PHA and a PHB are intracellularly co-produced. Non-Patent Literature 5 reports that when a gene encoding a medium-chain-length PHA synthase derived from *Allochromatium vinosum* is introduced into *Ralstonia eutropha*, which synthesizes a PHB, the PHB and a medium-chain-length PHA are intracellularly co-produced.

CITATION LIST

Patent Literatures

PTL 1: JP H06-157878 A
PTL 2: JP H08-510498 A
PTL 3: WO 2002/50156
PTL 4: JP 2004-250629 A

Non-Patent Literatures

NPTL 1: Wing-Hin Lee, Ching-Yee-Loo, Christopher T. Nomura, Kumar Sudesh, Bioresource Technology, vol. 99, pp. 6844-6851, (2008)
NPTL 2: Hiromi Matsusaki, Sumihide Manji, Kaunori Taguchi, Mikiya Kato, Toshiaki Fukui, Yoshiharu Doi, Journal of Bacteriology, vol. 180, pp. 6459-6467, (1998)
NPTL 3: Arnulf Timm, David Byrom, Alexander Steinbuchel, Applied Microbiology and Biotechnology, vol. 33, pp. 296-301, (1990)
NPTL 4: Matthias Liebergesell, Frank Mayer, Alexander Steinbuchel, Applied Microbiology and Biotechnology, vol. 40, pp. 292-300, (1993)
NPTL 5: Kawalpreet K. Aneja, Richard D. Ashby, Daniel K. Y. Solaiman, Biotechnology Letters, vol. 31, pp. 1601-1612, (2009)

SUMMARY OF INVENTION

Technical Problem

An object of the present invention is to improve the crystallization speed of a PHA copolymer which is slowly crystallized to improve the melt workability of the PHA copolymer in working such as injection molding, film molding, blow molding, fiber spinning, extrusion foaming or bead foaming, thereby improving the resultant articles in productivity.

Solution to Problem

In order to solve the problems, the inventors have repeatedly made eager researches to find out that by using a microorganism having genes encoding two or more PHA synthases which are different from each other and are derived from the genus *Aeromonas*, three or more PHAs different in melting point from each other can be co-produced in the same cell thereof, and further the resultant PHA mixture can be remarkably improved in crystallization speed. Thus, the present invention has been achieved.

Accordingly, a first aspect of the present invention relates to a microorganism having genes encoding two or more PHA synthases which are different from each other and are derived from the genus *Aeromonas*. The genes encoding the PHA syntheses derived from the genus *Aeromonas* are preferably genes encoding at least two PHA synthases which are capable of synthesizing a copolymer PHA including, as its monomer unit species, 3HB and 3HH and which are different in substrate specificity toward 3HH from each other. Moreover, the genes encoding the PHA synthases derived from the genus *Aeromonas* are each preferably selected from the group consisting of a gene encoding a PHA synthase which has an amino acid sequence shown in SEQ ID NO: 1, and a gene encoding a protein which has a sequence homology of 90% or more to the amino acid sequence and which has PHA synthase activity. Furthermore, one or ones of the genes that encode, out of the PHA synthases, a PHA synthase having a higher substrate specificity toward 3HH is/are preferably a gene encoding a protein which has an amino acid sequence in which $149^{th}$ asparagine in the amino acid sequence shown in SEQ ID NO: 1 is substituted with serine, and/or a gene encoding a protein which has an amino acid sequence in which $171^{th}$ aspartic acid in the amino acid sequence shown in SEQ ID NO: 1 is substituted with glycine. One of the genes that encodes, out of the PHA synthases, a PHA synthase having a lower substrate specificity toward 3HH is preferably a gene encoding a protein which has the amino acid sequence shown in SEQ ID NO: 1, or a gene encoding a protein which has an amino acid sequence in which $505^{th}$ alanine in the amino acid sequence shown in SEQ ID NO: 1 is substituted with an amino acid other than alanine. Furthermore, the microorganism is a microorganism having a gene encoding a PHA synthase derived from the genus *Cupriavidus*. The microorganism of the invention is preferably a transformant in which a host is a microorganism belonging to the genus *Cupriavidus*. The microorganism belonging to the genus *Cupriavidus* is preferably *Cupriavidus necator*. The microorganism preferably further has a gene encoding R-body-specific enoyl-CoA hydratase to enhance the expression of the gene encoding R-body-specific enoyl-CoA hydratase.

A second aspect of the present invention relates to a method for producing a PHA mixture, including the step of culturing the above-defined microorganism to produce three or more PHAs different in melting point from each other in a cell of the microorganism. One or more PHAs included in the PHA mixture are (each) a copolymer PHA containing, as its monomer unit species, at least 3-hydroxybutyric acid and 3-hydroxyhexanoic acid. Furthermore, the following are each preferred: out of the PHAs included in the PHA mixture, a PHA having the highest melting point is a PHA showing an endothermic peak at 160 to 185° C. in a DSC yielded by annealing the mixture at 160° C.; out of the PHAs included in the PHA mixture, a PHA having the lowest melting point is a PHA showing an endothermic peak at 90 to 135° C. in a DSC of the mixture and out of the PHAs included in the PHA mixture, at least one PHA having a middle melting point is a PHA showing an endothermic peak at 136 to 155° C. in a DSC yielded by annealing the mixture at 130° C.

Advantageous Effects of Invention

The present invention makes it possible to improve a PHA copolymer, the crystallization of which is slow, in crystallization speed to improve the PHA copolymer in melt workability and working speed in a working such as injection molding, film molding, blow molding, fiber spinning, extrusion foaming or bead foaming.

DESCRIPTION OF EMBODIMENTS

Hereinafter, the present invention will be described in more detail.

The present invention relates to a microorganism having genes encoding two or more PHA syntheses which are different from each other and are derived from the genus *Aeromonas* (the microorganism win be abbreviated hereinafter to the "microorganism of the invention"). The PHA synthases derived from the genus *Aeromonas* may each be a wild type PHA synthase derived from the genus *Aeromonas*, or a modified PHA synthase produced by applying an artificial modification to a wild type PHA synthase derived from the genus *Aeromonas*.

The microorganism of the invention is not particularly limited as long as the microorganism has genes encoding two or more PHA synthases which are different from each other and are derived from the genus *Aeromonas*. The genes are each preferably a gene encoding a PHA synthase which is capable of synthesizing a copolymer PHA including, as its monomer unit species, 3HB and 3HH. In this case, these PHA synthases are preferably at least two PHA synthases different in substrate specificity toward 3HH from each other. In the document, a PHA synthase having a higher substrate specificity toward 3HH, out of the two PHA synthases different in substrate specificity toward 3HH from each other, is defined as a "PHA synthase A"; and a PHA synthase having a lower substrate specificity toward 3HH, out of the two PHA synthases, is defined as a "PHA synthase B". The wording "having a higher substrate specificity toward 3HH" referred to herein means that in the synthesis of a copolymer PHA, the PHA synthase concerned has a higher capability of taking 3HH into the copolymer as its monomer unit species than any other PHA synthase. When the microorganism of the invention has genes encoding three or more PHA synthases derived from the genus *Aeromonas*, the substrate specificity which the PHA synthase concerned shows toward 3HH may be used as a standard to divide these three or more enzymes appropriately into two groups and then regard one and the other of these groups as a PHA synthase A and a PHA synthase B, respectively. When the three or more enzymes include a PHA synthase having a middle substrate specificity, this PHA synthase may be handled as a PHA synthase different from the PHA synthase A and the PHA synthase B.

In the present invention, the gene encoding a PHA synthase A and the gene encoding a PHA synthase B are each preferably a gene encoding a PHA synthase having an amino acid sequence shown in SEQ ID NO: 1, or a gene encoding a protein which has a sequence homology of 90% or more, preferably 95% or more, more preferably 98% or more to the amino acid sequence and which has PHA synthase activity. In the invention, it is preferred to select the PHA synthase A and the PHA synthase B from the following and then use a combination of the synthases A and B: a wild type PHA synthase derived from the genus *Aeromonas caviae* and having the amino acid sequence shown in SEQ ID NO: 1; and modified PHA synthases each produced by subjecting the wild type PHA synthase to an artificial modification such as a substitution, insertion or deletion of an amino acid to change the substrate specificity of the PHA synthase to 3HH in accordance with the species of the modification, the degree thereof, and others.

The PHA synthase A is preferably higher in substrate specificity to 3HH than a wild type PHA synthase having the amino acid sequence shown in SEQ ID NO: 1 and derived from *Aeromonas caviae*, and is more preferably a modified PHA synthase yielded by introducing an artificial modification into the wild type PHA synthase to make the substrate specificity thereof to 3HH high. Examples of a gene encoding the PHA synthase A which the microorganism of the invention has include a gene encoding a protein which has an amino acid sequence in which $149^{th}$ asparagine in the amino acid sequence shown in SEQ ID NO: 1 is substituted with serine; and a gene encoding a protein which has an amino acid sequence in which $171^{th}$ aspartic acid in the amino acid sequence shown in SEQ ID NO: 1 is substituted with glycine. Particularly preferred is a gene encoding a protein which has an amino acid sequence in which $149^{th}$ asparagine in the amino acid sequence shown in SEQ ID NO: 1 is substituted with serine and further $171^{th}$ aspartic acid therein is substituted with glycine. An example of such a gene is a gene having a base sequence shown in SEQ ID NO: 13.

In the meantime, the PHA synthase B is preferably equivalent or less than in substrate specificity to 3HH than the wild type PHA synthase having the amino acid sequence shown in SEQ ID NO: 1. A specific and preferred example of a gene encoding the PHA synthase B is a gene encoding a wild type PHA synthase having an amino acid sequence shown in SEQ ID NO: 1, or a gene encoding a modified PHA synthase yielded by introducing an artificial modification into the same wild type PHA synthase to make the substrate specificity thereof to 3HH equivalent or low. A specific example of the latter is preferably gene encoding a protein which has an amino acid sequence in which $505^{th}$ alanine in the amino acid sequence shown in SEQ ID NO:

1 is substituted with an amino acid other than alanine. The other amino acid is, for example, tryptophan.

The method for causing the same cell of the microorganism of the invention to have and keep genes encoding two or more PHA syntheses derived from the genus *Aeromonas* is not particularly limited. The microorganism of the invention has not yet been discovered in the natural world. However, the microorganism of the invention can be produced by introducing the above-mentioned genes encoding the PHA syntheses into a microorganism that is to be a host, using, for example, a gene recombination technique. For example, using a microorganism belonging to the genus *Aeromonas* as a host, one or more genes (each) encoding another PHA synthase (PHA synthase different from a PHA synthase which the host has and keeps) derived from the genus *Aeromonas* may be introduced into the host. Alternatively using a microorganism belonging to a genus different from the genus *Aeromonas* as a host, two or more genes each encoding a PHA synthase derived from the genus *Aeromonas* may be introduced into the host. Moreover, the microorganism which is to be the host may have a gene encoding a PHA synthase derived from an organism belonging to a genus different from the genus *Aeromonas*. For example, two or more genes encoding PHA synthases derived from the genus *Aeromonas* are preferably introduced into a microorganism belonging to the genus *Cupriavidus*. In this case, a gene encoding a PHA synthase which a microorganism belonging to the genus *Cupriavidus* originally has may be present as it is, or disrupted or deleted.

The microorganism of the invention may have, besides the genes encoding two or more PHA syntheses derived from the genus *Aeromonas*, a gene encoding a PHA synthase derived from an organism belonging to a genus different from the genus *Aeromonas*. For example, the microorganism of the invention preferably has a gene encoding a PHA synthase derived from the genus *Cupriavidus*. The microorganism more preferably has a gene encoding a PHA synthase derived from *Cupriavidus necator* made of an amino acid sequence shown in SEQ ID NO: 2; or a gene encoding a protein which has a sequence homology of 90% or more, preferably 95% or more, more preferably 98% or more to the amino acid sequence and which has PHA synthase activity. In this way, the PHA copolymer can be improved in crystallization speed.

The microorganism of the invention may have the single gene encoding a PHA synthase derived from an organism belonging to a genus different from the genus *Aeromonas*, or have two or more genes each encoding the same PHA synthase as described just above.

In the case of introducing into a host, the gene(s) (each) encoding a PHA synthase derived from the genus *Aeromonas* or derived from an organism belonging to a genus different from the genus *Aeromonas*, the form that the microorganism of the invention has the PHA-synthase-encoding gene(s) may be a form that plasmid has the gene(s), or a form that the gene(s) has/have been introduced into any position of a chromosome of the microorganism. These forms may be used together with each other. In the case of the form that plasmid has the gene(s), plasmid may drop out when the organism is cultured; thus, the form is more preferably a form that the chromosome has thereon the gene(s).

The microorganism of the invention preferably has an transcriptional regulatory sequence for adjusting/controlling the expression of the above-mentioned genes each encoding a PHA synthase derived from the genus *Aeromonas* or derived from an organism belonging to a genus different from the genus *Aeromonas* at the upstream side of the gene. The transcriptional regulatory sequence is not particularly limited, and may be an transcriptional regulatory sequence which the host originally has, or may be an appropriate combination of two or more out of known promoters, a Shine-Dalgarno sequence (SD sequence), variants thereof, and others. Examples of the transcriptional regulatory sequence used for the genes encoding the PHA synthases in the microorganism of the invention include a lac promoter, a trp promoter shown in SEQ ID NO: 4, a lacUV5 promoter, a tac II promoter, a tic promoter, a trc promoter shown in SEQ ID NO: 5, a lacN15 promoter shown in SEQ ID NO 32 (variant of the lac promoter), a promoter (REP promoter) of a phaCAB operon derived from *Cupriavidus necator* and variants thereof any combination of, e.g., a promoter of a phaP1 gene encoding phasin derived from *Cupriavidus necator* with an SD sequence (REP-SD) of a phaC1 gene derived from *Cupriavidus necator*, which is shown in SEQ ID NO: 6, and variants thereof, and an expression regulatory sequence of a phaCAB operon derived from *Cupriavidus necator*, which is shown in SEQ ID NO: 3; and any other known transcriptional regulatory sequence. Furthermore, an transcriptional regulatory sequence is also usable which is obtained by modifying any one of these transcriptional regulatory sequences by deletion, substitution or insertion of a base. In the invention, the transcriptional regulatory sequence to be used is appropriately selected, thereby making it possible to adjust the presence amount of each of the PHA synthases in any cell of the microorganism, and control the production amount of each of the resultant PHA components and the proportion thereof.

The microorganism of the invention preferably father has a gene encoding R-body-specific enoyl-CoA hydratase. More preferably, this R-body-specific enoyl-CoA hydratase is enhanced. The method for enhancing R-body-specific enoyl-CoA hydratase is not particularly limited, and is preferably a method of enhancing the expression of the gene encoding R-body-specific enoyl-CoA hydratase. The method for enhancing the expression of the gene encoding R-body-specific enoyl-CoA hydratase is, for example, a method of substituting a promoter of a gene, which the host has, for encoding R-body-specific enoyl-CoA hydratase with a high expression promoter; or a method of inserting a high expression promoter to the upstream side of the gene. The promoter may be partially modified to enhance the expression. Alternatively, a gene encoding R-body-specific enoyl-CoA hydratase may be introduced into the host in such a manner that a plasmid has the gene, or that the gene is introduced into any position of a chromosome of the host. However, in the case of the manner that a plasmid has the gene, the plasmid may drop out when the microorganism is cultured. Thus, the manner that the chromosome has thereon the gene is more preferred. At this time, the gene encoding R-body-specific enoyl-CoA hydratase to be introduced may be a gene derived from the host or derived from an organism other than the host. Alternatively, a gene obtained by modifying this host-derived or host-not-derived gene artificially may be used. The introduction of such plural genes may be performed. When the host is, for example, *Cupriavidus necator*, three genes of phaJ4a, phaJ4b and phaJ4c are present as genes encoding R-body-specific enoyl-CoA hydratase on chromosomes of the host. The expression of one or more of these three can be enhanced. An example of the method for enhancing the expression is a method of inserting an transcriptional regulatory sequence composed of a high expression promoter and an SD sequence to a directly upstream site of phaJ4b. The expression regulatory sequence used in this case is, for example, an expression regulatory sequence of a phaCAB operon, which is shown in SEQ ID NO: 3. Alternatively, a trp promoter shown in SEQ ID NO: 4 or a trc promoter shown in SEQ ID NO: 5 may be used in the state of being linked to an SD sequence shown in SEQ ID NO: 6. The method for the introduction, insertion or substitution of such a DNA may be a known method. For example, for the substitution of a promoter present at a directly upstream site of a gene encoding R-body-specific enoyl-CoA hydratase present on a chromosome of a microorganism which is to be a host, or for the insertion of a different promoter into the directly upstream site, for example, a homologous recombination method is usable.

The host of the microorganism of the invention is not particularly limited. It is preferred to use, as the host, any microorganism belonging to the following: the genus *Acinetobacter*, the genus *Aeromonas*, the genus *Alcaligenes*, the genus *Allochromatium*, the genus *Azorhizobium*, the genus *Azotobacter*, the genus *Bacillus*, the genus *Burkholderia*, the genus *Candida*, the genus *Caulobacter*, the genus *Chromobacterium*, the genus *Comamonas*, the genus *Cupriavidus*, the genus *Ectothiorhodospira*, the genus *Escherichia*, the genus *Klebsiella*, the genus *Methylobacterium*, the genus *Nocardia*, the genus *Paracoccus*, the genus *Pseudomonas*, the genus *Ralstonia*, the genus *Rhizobium*, the genus *Rhodobacter*, the genus *Rhodococcus*, the genus *Rhodospirillum*, the genus *Rickettsia*, the genus *Saccharomyces*, the genus *Sinorhizobium*, the genus *Sphingomonas*, the genus *Synechocystis*, the genus *Thiococcus*, the genus *Thiocystis*, the genus *Vibrio*, the genus *Wautersia*, and the genus *Zoogloea*. The microorganism used as the host is more preferably any microorganism belonging to, out of these genera, the genus *Aeromonas*, the genus *Alcaligenes*, the genus *Cupriavidus*, the genus *Escherichia*, the genus *Pseudomonas* and the genus *Ralstonia*; is more preferably any microorganism belonging to the genus *Cupriavidus*, the genus *Escherichia*, and the genus *Ralstonia*; is even more preferably any microorganism belonging to the genus *Cupriavidus*; and is in particular preferably *Cupriavidus necator*.

The microorganism of the invention is cultured to produce, in cells thereof, three or more PHAs different in melting point from each other, and then the PHAs are recovered from the microbial cell body. In this way, a PHA mixture including the three or more PHAs different in melting point from each other can be produced.

A carbon source or carbon sources for cultivating the microorganism of the invention may be any carbon source as long as the PHA-producing microorganism of the invention is capable of assimilating the carbon source. The carbon source is preferably a saccharide such as glucose, fructose or sucrose; an oil and fat such as palm oil, palm kernel oil, corn oil, coconut oil, olive oil, soybean oil, rapeseed oil or Jatropha oil, or a fractional oil thereof or a purified byproduct thereof; a fatty acid such as lauric acid, oleic acid, stearic acid, palmitic acid or myristic acid, or a derivative thereof. The carbon source is more preferably a plant oil and fat such as palm oil or palm kernel oil; or palm olein, palm double olein or palm kernel olein, which is a low-melting-point fraction obtained by fractionating palm oil or palm kernel oil; or a purified byproduct of an oil and fat, such as a PFAD (palm fatty acid distillate), a PKFAD (palm kernel fatty acid distillate) or a fatty acid distilled product of rapeseed oil, particularly, from the viewpoint of avoiding the competition of this use of the carbon source with use thereof as food.

It is preferred in the production of the PHAs in the present invention to use a medium containing the carbon source, a nitrogen source, which is a nutrient source other than the carbon source, an inorganic salt, and any other organic nutrient source to culture the microorganism. Examples of the nitrogen source include ammonia, urea, and ammonium salts such as ammonium chloride, ammonium sulfate and ammonium phosphate, peptone, a meat extract, and a yeast extract. Examples of the inorganic salt include potassium dihydrogen phosphate, disodium hydrogen phosphate, magnesium phosphate, magnesium sulfate, and sodium chloride. Examples of the other organic nutrient source include amino acids such as glycine, alanine, serine, threonine and proline, and vitamins such as vitamins B1, B12 and C.

The culturing temperature, the culturing period, the pH at the time of the culturing, the medium, and other conditions may be culturing conditions as used ordinarily for the used microorganism.

In the present invention, the method for collecting the PHA mixture from the microbial cell body is not particularly limited and may be, for example, a method as described hereinafter. After the end of the culturing, from the culture liquid, the microbial cell body is separated by, for example, a centrifugal separator, and the microbial cell body is washed with, for example, distilled water and methanol and then dried. From this dry microbial cell body, an organic solvent such as chloroform is used to extract the PHA mixture. From this organic solvent solution containing the PHA mixture, any insoluble matter derived from the microbial cell body is removed by, for example, filtration. A poor solvent such as methanol or hexane is added to the resultant filtrate to precipitate the PHA mixture. Furthermore, the supernatant is removed by filtration or centrifugation, and the remnant is dried to collect the PHA mixture.

It is generally known that a PHA synthase functions in the form of a dimer. The microorganism of the invention has genes encoding two or more PHA synthases derived from the genus *Aeromonas*; thus, the resultant PHA synthase dimers may each be a homodimer composed of two molecules of the same PHA synthase, or may each be of one or more heterodimer species in (each of) which different two PHA synthases are combined with each other. In this case, the individual PHA synthase dimers have different substrate specificities. Accordingly PHAs produced by culturing the microorganism of the invention are a mixture of PHAs different in copolymerized-monomer ratio from each other (abbreviated hereinafter to the PHA mixture of the invention). The PHA mixture generally includes three or more PHAs different in melting point from each other. These PHAs produced by the PHA synthases derived from the genus *Aeromonas* are each preferably a copolymer PHA including, as its monomer unit species, at least 3HB and 3HH.

In the meantime, it does not happen that a PHA synthase derived from the genus *Aeromonas* is combined with a PHA synthase derived from an organism belonging to a genus different from the genus *Aeromonas* to produce a dimer. Accordingly, when the microorganism of the invention further has a gene encoding a PHA synthase derived from an organism belonging to a genus different from the genus *Aeromonas*, a different PHA is also produced which has a melting point different from the melting points of the PHAs produced by the PHA synthases derived from the genus *Aeromonas*. In this case, the PHA produced by the PHA synthase derived from an organism belonging to a genus different from the genus *Aeromonas* may be a PHB, which is a homopolymer made from 3HB, or may be a copolymer PHA, such as a PHBH or PHBV; and is preferably a PHB.

Out of the PHAs included in the PHA mixture of the invention, a PHA (A) having the highest melting point may be a copolymer PHA produced by the PHA synthases derived from the genus *Aeromonas*, or a PHB or a copolymer PHA produced by the PHA synthase derived from an organism belonging to a genus different from the genus *Aeromonas*. When the PHA (A) is a copolymer PHA, the PHA (A) may be a PHBH or PHBV or a copolymer other than the PHBH or PHBV. The PHA (A) contains, as its monomer unit species, 3HB in a proportion that is preferably 95% or more, more preferably 97% or more, even more preferably 99% or more by mole. The PHA (A) is preferably a PHA having a melting point of 160° C. or higher. However, when the PHA (A) contained in the PHA mixture is small in content by percentage, the PHA (A) may not have an evident endothermic peak in an ordinary DSC of the mixture. In this case, the PHA (A) is preferably a PHA showing an endothermic peak at 160 to 185° C. in a DSC of the PHA mixture after this mixture is annealed at 160° C. in accordance with a method in working examples that will be described later.

Out of the PHAs included in the PHA mixture of the invention, a PHA (B) having the lowest melting point is preferably a copolymer PHA, more preferably a copolymer PHA produced by the PHA synthases derived from the genus *Aeromonas*, even more preferably a copolymer PHA containing, as its monomer unit species, at least 3HB and 3HH. In this case, the PHA (B) contains, as its monomer unit species, 3HH in a proportion that is preferably 7% or more, more preferably 8% or more, even more preferably 10% or more by mole. Moreover, the PHA (B) preferably contains, as its monomer unit species, 3HB in a proportion of 80% or more by mole. The PHA (B) may contain, besides 3HB and 3HH, e.g., 3-hydroxypropionic acid, 3HV or 4-hydroxybutyric acid as its monomer unit species. The PHA (B) is more preferably a PHBH. The PHA (B) is preferably a PHA showing an endothermic peak at 90 to 135° C. in a DSC of the PHA mixture.

Out of the PHAs included in the PHA mixture of the invention, a PHA (C) showing a melting point between the respective melting points of the PHA (A) and the PHA (B) is preferably a copolymer PHA, more preferably a copolymer PHA produced by the PHA syntheses derived from the genus *Aeromonas*, even more preferably a copolymer PHA containing, as its monomer unit species, at least 3HB and 3HH. The PHA (C) may be a single(-species) PHA (C), or a mixture of two or more(-species) PHAs (C). The PHA (C) contains 3HB as one of the monomer unit species in a proportion that is preferably 90% or more, more preferably 92% or more, even more preferably 93% or more by mole of the whole of the PHA (C) (provided that when the PHA (C) is a mixture, the whole herein is the whole of the mixture). Moreover, the PHA (C) contains 3HH as another of the monomer unit species in a proportion that is preferably 3% or more, more preferably 4% or more, even more preferably 5% or more by mole of the whole of the PHA (C). The PHA (C) may contain, besides 3HB and 3HH, e.g., 3-hydroxypropionic acid, 3-hydroxyvaleric acid or 4-hydroxybutyric acid as a monomer unit species. The PHA (C) usually has a melting point between 136 and 155° C. as the middle melting point between the respective melting points of the PHA (A) and the PHA (B). When the content by percentage of the PHA (C) is low in the PHA mixture, the PHA (C) may not show any endothermic peak in an ordinary DSC of the mixture. In this case, the PHA (C) is preferably a PHA showing an endothermic peak at 136 to 155° C. in a DSC of the PHA mixture after this mixture is annealed at 130° C. in accordance with the method in the working examples, which will be described later.

In the PHA mixture of the invention, the PHA (B), which has the lowest melting point, is a main polymer component. The content by percentage of the PHA (A), which has the highest melting point, is not particularly limited, and is preferably from 0.01 to 10% by weight, more preferably from 0.05 to 8% by weight of 100% by weight of the total of the PHA (A), the PHA (B), and PHA (C). The content by percentage of the PHA (C), which has a middle melting point, is not particularly limited, either, and is preferably from 1 to 30% by weight, more preferably from 2 to 25% by weight of 100% by weight of the total of the PHA (A), the PHA (B), and PHA (C).

The PHA mixture produced by the present invention is a mixture improved in crystallization speed. The mixture may contain other additives, such as an antioxidant, an ultraviolet absorbent, colorants such as a dye and a pigment, a plasticizer, a lubricant, an inorganic filler, an antistatic agent, an anti-mold agent, an antibacterial agent, a foaming agent, and a flame retardant, as needed. The mixture may contain any other nucleating agent.

A resin composition obtained as described above can be formed/worked to be produced into a formed article. The method for the forming/working may be a method known in the prior art, such as injection molding, film molding, blow molding, fiber spinning, extrusion foaming, or bead foaming. The PHA mixture obtained by the production method of the present invention is unproved in crystallization speed, and is additionally a mixture in which three or more PHAs different in melting point from each other are dispersed at a molecular level; therefore, when this case according to the invention is compared with the case of producing a copolymer PHA, and a high-melting-point PHA, which is to be a nucleating agent, separately from each other and then blending the PHAs with each other, the nucleating agent in the former case can be finely dispersed by a simpler method and further the mixture can be formed/worked at a lower temperature, for example, a temperature of 170° C. or lower.

The formed article is usable for, for example, various containers, packaging members, films for agriculture and horticulture, and medical materials.

EXAMPLES

Hereinafter, the present invention will be more specifically described by demonstrating working examples thereof. However, the invention is never limited to these examples. The following were used about the breeding of any bacterial strain, the monomer composition analysis of any PHA, and a method for evaluating the crystallization of any PHA.

Breeding of Bacterial Strain:

Any genetic manipulation described in the working examples, production examples, reference examples, and comparative examples described in the document can be attained by methods described in Green, M. R. and Sambrook, J., 2012, Molecular Cloning: A Laboratory Manual Fourth Ed., Cold Spring Harbor Laboratory Press, Cold Spring Harbor, N.Y. Any enzyme, any cloning host and any other that are used in the genetic manipulation are commercially available from suppliers in the market, and are usable in accordance with their manual. Any enzyme used in the working examples and the others is not particularly limited as long as the enzyme is usable in genetic manipulation.

Analysis of Respective Copolymerization Proportions of Monomer Unit Species Contained in PHA:

The monomer composition analysis of a PHA or PHAs obtained was measured by gas chromatography. To about 20 mg of the resultant PHA or a mixture of the resultant PHAs were added 2 mL of a sulfuric-acid/methanol mixed liquid (15/85) and 2 mL of chloroform, and the system was air-tightly sealed. The system was heated at 100° C. for 140 minutes to subject the reactants to methyl esterification. After the system was cooled, 1.5 g of sodium hydrogen carbonate was added bit by bit to the reaction system to neutralize this system. The system was allowed to stand still until the generation of carbon dioxide was stopped. Thereto was added 4 mL of diisopropyl ether, and then the entire components were sufficiently mixed with one another, and then centrifuged. The composition of a methyl ester of 3HB and a methyl ester of 3HH in the supernatant was analyzed by capillary gas chromatography to calculate the proportion of the 3HH monomer. For the gas chromatography, the following were used: GC-17A manufactured by Shimadzu Corp.; and NEUTRA BOND-1 (column length: 25 m; column inside diameter 0.25 mm; and liquid membrane thickness: 0.4 μm) manufactured by GL Sciences Inc. as a capillary column. As a carrier gas, He was used. The inlet pressure of the column was set to 100 kPa, and the volume of a poured sample was set to 1 μL. About temperature conditions, the temperature was raised from a starting temperature of (100° C. to 200° C. at a rate of 8° C./minute, and further the temperature was raised from 200° C. to 290° C. at a rate of 30° C./minute. The copolymerization proportion of each monomer unit species contained, which is measured by this analysis method, is the average of the respective proportions in all the PHAs contained in the PHA mixture.

Evaluation of Crystallization of PHA:

The crystallization of any resultant PHA was evaluated by making a measurement using a differential scanning calorimeter (DSC 220, manufactured by SII Nanotechnology Inc.). In the differential scanning calorimetry, 2 to 5 mg of the PHA or a mixture of the PHAs was raised in temperature at 10° C./minute from 25° C. to 170° C., and then kept at 170° C. for 5 minutes. This sample was then cooled at 10° C./minute from 170° C. to 25° C. Thereafter, the sample was further kept at 25° C. for 5 minutes, and then raised in temperature again up to 170° C. at 10° C./minute. From the crystallization peak temperature (Tc) and the crystallization calorific value (Hc) in an exothermic curve of the sample that is obtained in the cooling, the easiness of the crystallization thereof was evaluated. As the sample is higher in crystallization peak temperature (Tc) and larger in crystallization calorific value (Hc), the sample is better in crystallization.

Measurement of Melting Point of PHA Component Having Melting Point of 90 to 135° C.:

The melting point of a low-melting-point component included in PHAs yielded by purification after a microorganism was cultured was measured by the following method: 2 to 5 mg of the PHAs or a mixture thereof was raised in temperature at 10° C./minute from 25° C. to 170° C. in a differential scanning calorimetry thereof, and then kept at 170° C. for 5 minutes. This sample was then cooled at 10° C./minute from 170° C. to 25° C. Thereafter, the sample was further kept at 25° C. for 5 minutes, and then raised in temperature again up to 170° C. at 10° C./minute. In its endothermic curve obtained at the second temperature-raising time, a PHA having a peak having a peak top from 90 to 135° C. was determined to be the low-melting-point component, and the peak top temperature thereof was defined as the melting point (Tm—Low) thereof.

Measurement of Melting Point and Content by Percentage of PHA Component Having Melting Point of 160 to 185° C. by Annealing Method:

About PHAs yielded by purification after a microorganism was cultured, a differential scanning calorimeter was used to evaluate thereof by the following method:

In a DSC, 4.5 to 5.5 mg of the PHAs or a mixture thereof was raised in temperature at 10° C./minute from 23° C. to 160° C., and then kept at 160° C. for 30 minutes. In this way, this sample was annealed. The sample was then cooled at 10° C./minute down to 23° C. Thereafter, the sample was raised in temperature from 23° C. to 200° C. at 10° C./minute. During this period, a DSC curve of the sample was obtained. In the DSC curve obtained at the second temperature-raising period, about an endothermic peak having a peak top from 160 to 185° C., the endothermic peak calorie was measured. The peak top temperature thereof was defined as the melting point (Tm—High) of a high-melting-point component.

By comparing the endothermic peak calorie measured by the above-mentioned method with a separately prepared analytical curve, the content by percentage of the PHA component having a melting point of 160 to 185° C. in the PHA mixture was presumed. The method for preparing the analytical curve is as follows:

In the same way as in Comparative Example 1, which will be described later, a PHBH (3HH copolymerization proportion: 10.4% by mole) was produced. Moreover, a PHB was also produced in the same way as in Comparative Example 3. Next, the resultant PHBH and PHB were mixed with each other. In the following way, a PHBH/PHB mixture was produced in which a co-product was simulatively reproduced: Initially, each of the PHBH and the PHB were dissolved into chloroform to give a concentration of 10 g/L. In this way, respective solutions of these polymers were yielded. Next, the individual polymer solutions were mixed with each other to set the ratio by weight of the PHBH to the PHB to 90:10. To 400 ml of hexane was gently added 100 mL of the mixed polymer solution while hexane was stirred. The precipitated polymer was separated through filtration, and then dried at 60° C. to yield a PHBH/PHB mixture. In the same way, PHBH/PHB mixtures were yielded in which the respective ratios by weight of the PHBH to the PHB were 93:7, 85:15, and 80:20. The resultant four PHBH/PHB mixture species were each subjected to DSC to measure the melting calorie in a part of the measured temperature range that was higher than 160° C. From the resultant melting calorie in the part higher than 160° C., the above-mentioned analytical curve was prepared for presuming the PHB content by percentage in any PHA mixture.

Measurement of Melting Point and Content by Percentage of PHA Component Having Melting Point of 136 to 155° C. by Annealing Method:

A differential scanning calorimeter was used to evaluate PHAs yielded by purification after a microorganism was cultured by an annealing method in the following way:

In a DSC, 4.5 to 5.5 mg of the PHAs or a mixture thereof was raised in temperature at 10° C./minute from 23° C. to 130° C. and then kept at 130° C. for 30 minutes. In this way, this sample was annealed. The sample was then cooled at 10° C./minute down to 23° C. Thereafter, the sample was raised in temperature from 23° C. to 200° C. at 10° C./minute. During this period, a DSC curve of the sample was obtained. In the DSC curve obtained at the second temperature-raising period, about an endothermic peak having a peak top from 136 to 155° C., the endothermic peak calorie was measured. The peak top temperature thereof was defined as the melting point (Tm—Mid) of a middle-melting-point component.

The endothermic peak calorie measured by the above-mentioned method was compared with a separately prepared analytical curve. In this way, the content by percentage of the PHA component having a melting point of 136 to 155° C., which was included in the PHA mixture, was presumed. The method for preparing the analytical curve is as follows:

In the same way as in Comparative Example 1, which will be described later, a PHBH-A (3HH copolymerization proportion: 10.4% by mole) was produced. Moreover, a PHBH-B (3HH copolymerization proportion: 5.0% by mole) was also produced in the same way as in Comparative Example 2. Next, about the resultant PHBH-A, the above-mentioned analyzing method was used to measure the calorie of an endothermic peak having a peak top as a melting point in a range of 136 to 155° C. In the same way, about the PHBH-B also, a measurement was made about the endothermic peak calorie having a peak top as a melting point in a range of 136 to 155° C. It was supposed that the content by percentage of the PHA component included in the PHBH-A and having a melting point of 136 to 155° C. was 0% by weight, and that of the PHA component included in the PHBH-B and having a melting point of 136 to 155° C. was 100% by weight, the above-mentioned analytical curve was prepared.

Production Example 1: Production of KNK-005 REP-phaJ4b ΔphaZ1,2,6 Strain

First, in order to insert an expression regulatory sequence for enhancing the expression of a phaJ4b gene on a chromosome into an upstream site of the phaJ4b gene, a plasmid for expression regulatory sequence insertion was produced. A genome DNA of a C. necator H16 strain was used as a template to conduct a PCR using respective DNAs shown in SEQ ID NOs: 7 and 8 as a primer pair. As a polymerase therefor, a polymerase KOD-plus (manufactured by Toyobo Co., Ltd.) was used. In the same way, a PCR was conducted, using respective DNAs shown in SEQ ID NOs: 9 and 10 as a primer pair. Furthermore, in the same way, a PCR was conducted, using respective DNAs shown in SEQ ID NOs: 11 and 12 as a primer pair. A PCR was conducted, using the three DNA fragment species yielded by the PCRs described above as templates and using respective DNAs shown in SEQ ID NOs: 7 and 10 as a primer pair, and the resultant fragment was digested with SmiI. This DNA fragment was ligated with a DNA fragment obtained by digesting a vector pNS2X-sacB described in JP 2007-259708 A with SmiI, using a DNA ligase (manufactured by Toyobo Co., Ltd.) to produce a plasmid pNS2X-sacB+phaJ4bU-REP-phaJ4b, for expression regulatory sequence insertion, having a DNA sequence at the upstream side of the gene phaJ4b, an expression regulatory sequence composed of a phaC1 promoter and a phaC1SD sequence, and a phaJ4b gene sequence.

Next, an transcriptional regulatory sequence inserted strain was produced. The plasmid pNS2X-sacB+phaJ4bU-REP-phaJ4b, for transcriptional regulatory sequence insertion, was introduced into an E. coli S17-1 strain (ATCC47055). The E. coli strain and a KNK-005 ΔphaZ1,2,6 strain (see WO 2014/065253) were mix-cultured on a nutrient agar medium (manufactured by DIFCO) to be subjected to conjugal transfer. The KNK-005 ΔphaZ1,2,6 strain is a bacterial strain having a PHA synthase gene having a base sequence shown in SEQ ID NO: 13, a host of this strain being the C. necator H16 strain, and is further a bacterial strain in which phaZ1, phaZ2 and phaZ6, which are genes encoding PHA degrading enzymes, were disrupted.

From bacterial strains after the conjugal transfer, the following strain was selected: a bacterial strain growing on a Simmons' agar medium containing 250 mg/L of kanamycin sulfate (the medium including sodium citrate: 2 g/L, sodium chloride: 5 g/L, magnesium sulfate heptahydrate: 0.2 g/L, ammonium dihydrogen phosphate: 1 g/L, dipotassium hydrogen phosphate: 1 g/L, and agar: 15 g/L pH: 6.8). In this way, a strain was obtained in which the plasmid was incorporated into chromosomes of the KNK-005 ΔphaZ1,2,6 strain. Two generations of this strain were cultured on a nutrient broth medium (manufactured by DIFCO). Thereafter, bacterial strains growing on a nutrient agar medium containing 15% of sucrose were selected therefrom. From the resultant bacterial strains, a PCR was used to screen strains in which the expression regulatory sequence composed of the phaC1 promoter and the phaC1 SD sequence was inserted into a directly upstream site of the phaJ4b gene. One of the strains was named a KNK-005 REP-phaJ4b ΔphaZ1,2,6 strain. The KNK-005 REP-phaJ4b ΔphaZ1,2,6 strain is a bacterial strain in which the entire length of the phaZ1 gene and that of the phaZ6 gene on any chromosome thereof are deleted; codons from the $16^{th}$ codon to the termination codon of the phaZ2 gene are deleted; the chromosome has, thereon, a PHA synthase gene having a base sequence shown in SEQ ID NO: 13; and the expression regulatory sequence composed of the phaC1 promoter (REP promoter) and the phaC1 SD (REP-SD) sequence is inserted into the directly upstream site of the phaJ4b gene.

Production Example 2: Production of KNK-005 REP-phaJ4b ΔphaZ1::PlacN15SDM-phaC$_{Re}$ ΔphaZ2,6 Strain In order to introduce a PHB-producing gene expression cassette into a phaZ1-gene-deleted region of the KNK-005 REP-phaJ4b ΔphaZ1,2,6 strain produced in Production Example 1, a DNA-inserting plasmid was produced. First, a genome DNA of a C. necator H16 strain was used as a template to conduct a PCR using respective DNAs shown in SEQ ID NOs: 14 and 15 as a primer pair. In the same way, a PCR was conducted, using respective DNAs shown in SEQ ID NOs: 16 and 17 as a primer pair. The two DNA fragment species yielded by the PCRs were used as a template to conduct a PCR using respective DNAs shown in SEQ ID NOs: 14 and 17 as a primer pair. The resultant fragment was digested with SmiI. This DNA fragment was then ligated with a DNA fragment obtained by digesting pNS2X-sacB with SmiI, using a DNA ligase, to produce a plasmid pNS2X-sacB-dZ1UL, for DNA insertion, having a DNA sequence at the upstream side of the phaZ1 gene, a DNA sequence shown in SEQ ID NO: 18, and a DNA sequence at the downstream side of the phaZ1 gene.

Next, a genome DNA of a C. necator H16 strain was used as a template to conduct a PCR using respective DNAs shown in SEQ ID NOs: 19 and 20 as a primer pair. The resultant fragment was digested with MunI and SpeI. This DNA fragment was ligated with a DNA fragment obtained by digesting a pNS2X-sacB-dZ1UL with MunI and SpeI, using a DNA ligase, to produce a plasmid pNS2X-sacB-dZ1UL-SDM-phaC$_{Re}$, for DNA insertion, having a DNA sequence at the upstream side of the phaZ1 gene, the expression regulatory sequence composed of a modified SD sequence REP-SDM shown in SEQ ID NO: 21, a phaC$_{Re}$ gene sequence, and a DNA sequence at the downstream side of the phaZ1 structural gene.

Next, a product pCR®2.1-TOPO® (manufactured by a company Invitrogen) was used as a template to conduct a PCR using respective DNAs shown in SEQ ID NOs: 22 and 23 as a primer pair. In the same way, a PCR was conducted, using respective DNAs shown in SEQ ID NOs: 24 and 25 as a primer pair. Two DNA fragment species yielded by the PCRs were used as a temple to conduct a PCR using respective DNAs shown in SEQ ID NOs: 22 and 25 as a primer pair. The resultant fragment was digested with MunI. This DNA fragment was ligated with a DNA fragment obtained by digesting pNS2X-sacB-dZ1UL-SDM-phaC$_{Re}$ with MunI, using a DNA ligase. In this way, a plasmid pNS2X-sacB-dZ1UL-PlacN15SDM-phaC$_{Re}$, for DNA insertion, having a DNA sequence at the upstream side of the phaZ1 gene, an transcriptional regulatory sequence composed of a lacN15 promoter and REP-SDM, a phaC$_{Re}$ gene sequence, and a DNA sequence at the downstream side of the phaZ1 gene. The lacN15 promoter is a modified promoter having a base sequence shown in SEQ ID NO: 32, and is further a promoter yielded by modifying a spacer region of a lac promoter derived from Escherichia coli to weaken the expression enhancement of the promoter.

In the same way as used in the insertion of the above-mentioned expression regulatory sequence, a KNK-005 REP-phaJ4b ΔphaZ1,2,6 strain was used as a parent strain to insert a gene-expressing cassette for PHB production into a phaZ1-gene-deleted region thereof, using pNS2X-sacB-dZ1UL-PlacN15SDM-phaC$_{Re}$. The resultant strain was named a KNK-005 REP-phaJ4b ΔphaZ1::PlacN15SDM-phaC$_{Re}$ ΔphaZ2,6 strain. The KNK-005 REP-phaJ4b ΔphaZ1::PlacN15SDM-phaC$_{Re}$ ΔphaZ2,6 strain is a bacterial strain in which the entire length of the phaZ1 gene and that of the phaZ6 gene on any chromosome thereof are deleted; codons from the 16$^{th}$ codon to the termination codon of the phaZ2 gene are deleted; the expression regulatory sequence composed of the REP promoter and the REP-SD sequence is inserted into the directly upstream site of the phaJ4b gene; the lacN15 promoter, the REP-SDM sequence, and the phaC$_{Re}$ structural gene sequence, which is a gene encoding a PHA synthase derived from Cupriavidus necator, are inserted to the phaZ1-gene-deleted region; and the chromosome has thereon a PHA synthase gene having a base sequence shown in SEQ ID NO: 13.

Production Example 3: Production of KNK-005 REP-phaJ4b ΔphaZ1::Plac-phaC$_{Re}$ ΔphaZ2,6 Strain In order to introduce a PHB-producing gene expression cassette into a phaZ1-gene-deleted region of the KNK-005 REP-phaJ4b ΔphaZ1,2,6 strain produced in Production Example 1, a plasmid for DNA insertion was produced. First, a genome DNA of a C. necator H16 strain was used as a template to conduct a PCR using respective DNAs shown in SEQ ID NOs: 26 and 20 as a primer pair. The resultant fragment was digested with MunI and SpeI. This DNA fragment was then ligated with a DNA fragment obtained by digesting the pNS2X-sacB-dZ1UL produced in Production Example 1 with MunI and SpeI, using a DNA ligase, to produce a plasmid pNS2X-sacB-dZ1UL-SD-phaC$_{Re}$, for DNA insertion, having a DNA sequence at the upstream side of the phaZ1 gene, an expression regulatory sequence composed of an SD sequence REP-SD shown in SEQ ID NO: 6, a phaC$_{Re}$ gene sequence, and a DNA sequence at the downstream side of the phaZ1 gene.

Next, the product pCR®2.1-TOPO® was used as a template to conduct a PCR using respective DNAs shown in SEQ ID NOs: 27 and 25 as a primer pair. The resultant fragment was digested with EcoRI and MunI. This DNA fragment was ligated with a DNA fragment obtained by digesting pNS2X-sacB-dZ1UL-SD-phaC$_{Re}$ with MunI, using a DNA ligase, to produce a plasmid pNS2X-sacB-dZ1UL-Plac-phaC$_{Re}$, for DNA insertion, having a DNA sequence at the upstream side of the phaZ1 gene, the expression regulatory sequence composed of a lac promoter and REP-SD, the phaC$_{Re}$ gene sequence, and a DNA sequence at the downstream side of the phaZ1 gene.

In the same way as in Production Example 1, a KNK-005 REP-phaJ4b ΔphaZ1,2,6 strain was used as a parent strain to insert a gene-expressing cassette for PHB production into a phaZ1-gene-deleted region thereof using pNS2X-sacB-dZ1UL-Plac-phaC$_{Re}$. The resultant strain was named a KNK-005 REP-phaJ4b ΔphaZ1::Plac-phaC$_{Re}$ ΔphaZ2,6 strain. The KNK-005 REP-phaJ4b ΔphaZ1::Plac-phaC$_{Re}$ ΔphaZ2,6 strain is a bacterial strain in which the entire length of the phaZ1 gene and that of the phaZ6 gene on any chromosome thereof are deleted; codons from the 16$^{th}$ codon to the termination codon of the phaZ2 gene are deleted; the expression regulatory sequence composed of the REP promoter and the REP-SD sequence is inserted into the directly upstream site of the phaJ4b gene; the lac promoter, the REP-SD sequence, and the phaC$_{Re}$ structural gene sequence are inserted into the phaZ1-gene-deleted region; and the chromosome has thereon a PHA synthase gene having a base sequence shown in SEQ ID NO: 13.

Production Example 4: Production of Plasmid pCUP2-REP-phaC$_{Ac}$ for phaC$_{Ac}$ Expression A plasmid was produced for expressing a gene phaC$_{Ac}$ encoding a wild type PHA synthase derived from Aeromonas caviae. First, a genome DNA of a C. necator H16 strain was used as a template to conduct a PCR using respective DNAs shown in SEQ ID NOs: 28 and 29 as a primer pair. Next, a genome DNA of an A. caviae strain was used as a temple to conduct a PCR, using respective DNAs shown in SEQ ID NOs: 30 and 31 as a primer pair. A PCR was conducted, using the two DNA fragment species yielded by the PCRs described above as templates and using respective DNAs shown in SEQ ID NOs: 28 and 31 as a primer pair. The resultant fragment was digested with EcoRI and SpeI. This DNA fragment was ligated with a DNA fragment obtained by digesting a pCUP2 vector described in JP 2007-259708 A with MunI and SpeI, using a DNA ligase, to produce a plasmid pCUP2-REP-phaC$_{A}$, for phaC$_{Ac}$ expression, having an expression regulatory sequence composed of a REP promoter and REP-SD, and a phaC$_{Ac}$ gene sequence.

Production Example 5: Production of phaC$_{Ac}$-Expressing Plasmid Introduced Strain, Using KNK-005 REP-phaJ4b ΔphaZ1,2,6 Strain Described in Production Example 1 as Parent Strain The KNK-005 REP-phaJ4b ΔphaZ1,2,6 strain produced in Production Example 1 was cultured overnight in a nutrient broth medium. Into 100 mL of a nutrient broth medium was inoculated 0.5 mL of the resultant culture liquid, and then the strain was cultured at 30° C. for 3 hours. The resultant culture liquid was rapidly cooled on ice. The microbial cell body was collected and sufficiently washed with ice-cooled distilled water. Thereafter, the resultant microbial cell body was suspended in 2 mL of distilled water. The microbial cell body liquid was mixed with the pCUP2-REP-phaC$_{Ac}$ plasmid solution produced in Production Example 4. The mixture was poured into a cuvette to be electroporated. The electroporation was performed, using a Micro Pulser Electroporator (manufactured by Bio-Rad Laboratories, Inc.) under conditions of a voltage of 1.5 kV, a resistance of 800Ω, and a current of 25 μF. After the electroporation, the microbial cell body solution was collected, and thereto was added 5 mL of a nutrient broth medium to culture the microbial cell body at 30° C. for 3 hours. The resultant culture liquid was applied to a nutrient agar medium containing 100 mg/L of kanamycin sulfate. This was cultured at 30° C. for 3 days. From the resultant colonies, a bacterial strain into which pCUP2-REP-phaC$_{Ac}$ was introduced was obtained. The resultant bacterial strain was named a KNK-005 REP-phaJ4b ΔphaZ1,2,6/pCUP2-REP-phaC$_{Ac}$ strain.

Production Example 6: Production of phaC$_{Ac}$-Expressing Plasmid Introduced Strain, Using KNK-005 REP-phaJ4b ΔphaZ1::PlacN15SDM-phaC$_{Re}$ ΔphaZ2,6 Strain Described in Production Example 2 as Parent Strain In the same way as in Production Example 5, pCUP2-REP-phaC$_{Re}$ produced in Production Example 4 was introduced into the KNK-005 REP-phaJ4b ΔphaZ1::PlacN15SDM-phaC$_{Re}$ ΔphaZ2,6 strain produced in Production Example 2. The resultant bacterial strain was named a KNK-005 REP-phaJ4b ΔphaZ1::PlacN15SDM-phaC$_{Re}$ phaZ2,6/pCUP2-REP-phaC$_{Ac}$ strain.

Production Example 7: Production of phaC$_{Ac}$-Expressing Plasmid Introduced Strain, Using KNK-005 REP-phaJ4b ΔphaZ1::Plac-phaC$_{Re}$ ΔphaZ2,6 Strain Described in Production Example 3 as Parent Strain In the same way as in Production Example 5, pCUP2-REP-phaC$_{Ac}$ produced in Production Example 4 was introduced into the KNK-005 REP-phaJ4b ΔphaZ1::Plac-phaC$_{Re}$ ΔphaZ2,6 strain produced in Production Example 3. The resultant bacterial strain was named a KNK-005 REP-phaJ4b ΔphaZ1::Plac-phaC$_{Re}$ ΔphaZ2,6/pCUP2-REP-phaC$_{Ac}$ strain.

Reference Example 1: Production of PHA Mixture by Strain KNK-005 REP-phaJ4b ΔphaZ1::PlacN15SDM-phaC$_{Re}$ ΔphaZ2,6

The KNK-005 REP-phaJ4b ΔphaZ1::PlacN15SDM-phaC$_{Re}$ ΔphaZ2,6 strain produced in Production Example 2 was cultured and purified under conditions described below to produce a PHA mixture. About the resultant PHA mixture, the respective copolymerization proportions of its monomer units were measured, and further an annealing method was used to calculate out the presumed content by percentage of its PHA component having a melting point of 136 to 155° C., and that of its PHA component having a melting point of 160 to 185° C. The results are shown in Table 1. About the resultant PHA mixture, the crystallization speed was also evaluated. The result is shown in Table 2.

Culturing:

The bacterial strain was cultured as follows:

The composition of the seed medium was adjusted to 10 g/L of a meat extract, 10 g/L of bacto tryptone, 2 g/L of a yeast extract, 9 g/L of disodium hydrogen phosphate dodecahydrate, and 1.5 g/L of potassium dihydrogen phosphate. The pH thereof was set to 6.8.

The composition of the preculture medium was adjusted to 11 g/L disodium hydrogen phosphate dodecahydrate, 1.9 g/L of potassium dihydrogen phosphate, 12.9 g/L of ammonium sulfate, 1 g/L of magnesium sulfate heptahydrate, 5 mL/L of a solution of trace metals (solution obtained by dissolving, into 0.1 N hydrochloric acid, 16 g/L of iron(III) chloride hexahydrate, 10 g/L of calcium chloride dihydrate, 0.2 g/L of cobalt chloride hexahydrate, 0.16 g/L of copper sulfate pentahydrate, and 0.12 g/L of nickel chloride hexahydrate), and 50 mg/L of kanamycin. As the carbon source, palm double olein oil was used at a concentration of 25 g/L.

The composition of the PHA producing medium was adjusted to 5.78 g/L of disodium hydrogen phosphate dodecahydrate, 1.01 g/L of potassium dihydrogen phosphate, 4.37 g/L of ammonium sulfate, 1.5 g/L of magnesium sulfate heptahydrate, and 7.5 mL/L of a solution of trace metals (solution obtained by dissolving, into 0.1 N hydrochloric acid, 16 g/L of iron(II) chloride hexahydrate, 10 g/L of calcium chloride dihydrate, 0.2 g/L of cobalt chloride hexahydrate, 0.16 g/L of copper sulfate pentahydrate, and 0.12 g/L of nickel chloride hexahydrate). As the carbon source, palm single olein oil was used.

Into 10 mL of the seed medium was inoculated 50 μL of each glycerol stock of the bacterial strain, and the strain was cultured for 24 hours. The resultant was inoculated in an amount of 1.0% (v/v) into a 3-L jar fermenter (MDL-300 model, manufactured by B. E. Marubishi Co., Ltd.) into which 1.8 L of the preculture medium was put. The driving conditions were set as follows: a culturing temperature of 30° C., a stirring speed of 500 rpm, and an air flow rate of 1.8 L/minute. While the pH was controlled between 6.7 and 6.8, the strain was cultured for 28 hours. For the pH control, a 7% aqueous ammonium hydroxide solution was used.

PHA production and culturing were conducted as follows: First, the precultured yeast was inoculated in an amount of 25% (v/v) into a 10-L jar fermenter (MDL-1000 model, manufactured by B. E. Marubishi Co., Ltd.) into which 2 L of the PHA producing medium was put. The driving conditions were set as follows: a culturing temperature of 32° C., a stirring speed of 450 rpm, and an air flow rate of 3.0 L/minute. The pH was controlled between 6.7 and 6.8. For the pH control, a 7% aqueous ammonium hydroxide solution was used. The culturing was continued for 45 to 54 hours.

Purification:

When the culturing was ended, the culture broth was sampled. The microbial cell body was collected therefrom by centrifugation, washed with ethanol, and then vacuum-dried to give a dry cell body.

To 1 g of the resultant dry cell body was added 100 mL of chloroform, and the resultant was stirred at room temperature for a whole day and night to extract PHAs inside the microbial cell body. The microbial cell body residue was filtrated off, and then an evaporator was used to concentrate the PHAs to a total volume of 30 mL. Thereafter, the concentrated liquid was slowly added to 90 mL of hexane, and then the resultant was gently stirred for 1 hour. The precipitated PHAs were separated by filtration, and then vacuum-dried at 50° C. for 3 hours to give the PHAs as purified PHAs.

Reference Example 2: Production of PHA Mixture by KNK-005 REP-phaJ4b ΔphaZ1::Plac-phaC$_{Re}$ ΔphaZ2,6 Strain A PHA mixture was produced in the same way as in Reference Example 1 except that instead of the KNK-005 REP-phaJ4b ΔphaZ1::PlacN155SDM-phaC$_{Re}$ ΔphaZ2,6 strain, the KNK-005 REP-phaJ4b ΔphaZ1::Plac-phaC$_{Re}$ ΔphaZ2,6 produced in Production Example 3 was used. About the resultant PHA mixture, the respective copolymerization proportions of its monomer unit species were measured, and further an annealing method was used to calculate out the presumed content by percentage of its PHA component having a melting point of 136 to 155° C., and that of its PHA component having a melting point of 160 to 185° C. The results are shown in Table 1. About the resultant PHA mixture, the crystallization speed was also evaluated. The result is shown in Table 2.

Example 1: Production of PHA Mixture by KNK-005 REP-phaJ4b ΔphaZ1,2,6/pCUP2-REP-phaC$_{Ac}$ Strain A PHA mixture was produced in the same way as in Reference Example 1 except that instead of the KNK-005 REP-phaJ4b ΔphaZ1::PlacN15SDM-phaC$_{Re}$ ΔphaZ2,6 strain, the KNK-005 REP-phaJ4b ΔphaZ1,2,6/pCUP2-REP-phaC$_{Ac}$ strain produced in Production Example 5 was used. However, the used seed medium was a medium to which kanamycin sulfate was added to give a concentration of 50 mg/L. About the resultant PHA mixture, the respective copolymerization proportions of its monomer unit species were measured and further an annealing method was used to calculate out the presumed content by percentage of its PHA component having a melting point of 136 to 155° C., and that of its PHA component having a melting point of 160 to 185° C. The results are shown in Table 1. About the resultant PHA mixture, the crystallization speed was also evaluated. The result is shown in Table 2.

Example 2: Production of PHA Mixture by KNK-005 REP-phaJ4b ΔphaZ1::PlacN15SDM-phaC$_{Re}$, ΔphaZ2,6/pCUP2-REP-phaC$_{Ac}$ Strain A PHA mixture was produced in the same way as in Example 1 except that instead of the KNK-005 REP-phaJ4b ΔphaZ1,2,6/pCUP2-REP-phaC$_{Ac}$ strain, the KNK-005 REP-phaJ4b ΔphaZ1::PlacN15SDM-phaC$_{Re}$ ΔphaZ2,6/pCUP2-REP-phaC$_{Ac}$ strain produced in Production Example 6 was used. About the resultant PHA mixture, the respective copolymerization proportions of its monomer unit species were measured, and further an annealing method was used to calculate out the presumed content by percentage of its PHA component having a melting point of 136 to 155° C., and that of its PHA component having a melting point of 160 to 185° C. The results are shown in Table 1. About the resultant PHA mixture, the crystallization speed was also evaluated. The result is shown in Table 2.

Example 3: Production of PHA Mixture by KNK-005 REP-phaJ4b ΔphaZ1::Plac-phaC$_{Re}$, ΔphaZ2,6/pCUP2-REP-phaC$_{Ac}$ Strain A PHA mixture was produced in the same way as in Example 1 except that instead of the KNK-005 REP-phaJ4b ΔphaZ1,2,6/pCUP2-REP-phaC$_{Ac}$ strain, the KNK-005 REP-phaJ4b ΔphaZ1::Plac-phaC$_{Re}$ ΔphaZ2,6/pCUP2-REP-phaC$_{Ac}$ strain produced in Production Example 7 was used. About the resultant PHA mixture, the respective copolymerization proportions of its monomer unit species were measured, and further an annealing method was used to calculate out the presumed content by percentage of its PHA component having a melting point of 136 to 155° C., and that of its PHA component having a melting point of 160 to 185° C. The results are shown in Table 1. About the resultant PHA mixture, the crystallization speed was also evaluated. The result is shown in Table 2.

Comparative Example 1: Production of PHBH by KNK-631 Strain

For the culture and production thereof, a KNK-631 strain (see WO 2009/145164) was used. The culture was conducted as follows:

The composition of the seed medium was adjusted to 10 g/L of a meat extract, 10 g/L of bacto tryptone, 2 g/L of a yeast extract, 9 g/L of disodium hydrogen phosphate dodecahydrate, 1.5 g/L of potassium dihydrogen phosphate, pH: 6.8, and 50 mg/L of kanamycin sulfate.

The composition of the preculture medium was adjusted to 11 g/L disodium hydrogen phosphate dodecahydrate, 1.9 g/L of potassium dihydrogen phosphate, 12.9 g/L of ammonium sulfate, 1 g/L of magnesium sulfate heptahydrate, 25 g/L of palm kernel oil olein, and 5 mL/L of a solution of trace metals (solution obtained by dissolving, into 0.1 N hydrochloric acid, 16 g/L of iron(III) chloride hexahydrate, 10 g/L of calcium chloride dihydrate, 0.2 g/L of cobalt chloride hexahydrate, 0.16 g/L of copper sulfate pentahydrate, and 0.12 g/L of nickel chloride hexahydrate).

The composition of the PHA producing medium was adjusted to 3.85 g/L of disodium hydrogen phosphate dodecahydrate, 0.67 g/L of potassium dihydrogen phosphate, 2.91 g/L of ammonium sulfate, 1 g/L of magnesium sulfate heptahydrate, 5 mL/L of a solution of trace metals (solution obtained by dissolving into 0.1 N hydrochloric acid, 16 g/L of iron(III) chloride hexahydrate, 10 g/L of calcium chloride dihydrate, 0.2 g/L of cobalt chloride hexahydrate, 0.16 g/L of copper sulfate pentahydrate, and 0.12 g/L of nickel chloride hexahydrate), and 0.5 g/L of a product BIOSPUMEX 200K (antifoaming agent, manufactured by Cognis Japan Ltd.). As the carbon source, palm kernel oil olein was used, which is a low-melting-point fraction yielded by fractionizing palm kernel oil. An aqueous phosphate solution for feeding was a solution prepared to include 40 g/L of disodium hydrogen phosphate dodecahydrate, and 6.9 g/L of potassium dihydrogen phosphate.

Into the seed medium (10 mL) was inoculated a glycerol stock (50 μL) of the KNK-631 strain, and the strain was cultured for 24 hours. The strain was inoculated in an amount of 1.0% (v/v) into a 3-L jar fermenter (MDL-300 model, manufactured by B. E. Marubishi Co., Ltd.) into which 1.8 L of the preculture medium was put. The driving conditions were set as follows: a culturing temperature of 33° C., a stirring speed of 500 rpm, and an air flow rate of 1.8 L/minute. While the pH was controlled between 6.7 and 6.8, the strain was cultured for 28 hours. For the pH control, a 7% aqueous ammonium hydroxide solution was used.

Next, for the production and culture of PHAs, the precultured seed was inoculated in an amount of 5.0% (v/v) into a 10-L jar fermenter (MDL-1000 model, manufactured by B. E. Marubishi Co., Ltd.) into which 4.3 L of the PHA producing medium was put. The driving conditions were set as follows: a culturing temperature of 28° C., a stirring speed of 600 rpm, and an air flow rate of 6 L/minute. The pH was controlled between 6.7 and 6.8. For the pH control, a 14% aqueous ammonium hydroxide solution was used. Throughout the culture, palm kernel olein, as the carbon source, was fed to set the substrate supply specific rate into the range of 0.1 to 0.12 (oil-and-fat gram)×(net-dry-cell-body-weight gram)$^{-1}$×(h)$^{-1}$. The substrate supply specific rate is the quantity of oils and fats that are supplied per net cell body weight in any unit period, that is, a culture parameter defined as the oil and fat feeding rate per net dry cell body weight. The net dry cell body weight is the dry cell body weight obtained by subtracting, from the entire weight of the dry cell body, the weight of polyester contained therein. In short, the substrate supply specific rate is a value obtained in accordance with the following expression:

Substrate supply specific rate="oil and fat feeding rate (g/h)"/"net dry cell body weight (g)"="oil and fat supply quantity per unit period (g/h)"/ ("entire dry cell body weight (g)"−"polyester content (g)")

Moreover, after 20 hours from the start of the culture, an aqueous phosphate solution was continuously added to the medium to set the C/P ratio into the range of 600 to 800. The culture was performed for about 64 hours. In this way, the PHAs were produced. About the resultant PHAs, the respective copolymerization proportions of monomer unit species therein were measured, and further an annealing method was used to calculate out the presumed content by percentage of a PHA component having a melting point of 136 to 155° C. therein, and that of a PHA component having a melting point of 160 to 185° C. therein. The results are shown in Table 1. About the resultant PHAs, the crystallization speed was also evaluated. The result is shown in Table 2.

Comparative Example 2: Production of PHBH by KNK-005 Strain

A PHBH was produced in the same way as in Reference Example 1 except that instead of the KNK-005 REP-phaJ4b ΔphaZ1::PlacN15SDM-phaC$_{Re}$ ΔphaZ2,6 strain, a KNK-005 strain (see U.S. Pat. No. 7,384,766) was used. About the resultant PHBH, the respective copolymerization proportions of its monomer unit species were measured, and further an annealing method was used to calculate out the presumed content by percentage of its PHA component having a melting point of 136 to 155° C., and that of its PHA component having a melting point of 160 to 185° C. The results are shown in Table 1.

Comparative Example 3: Production of PHB by *C. necator* H16 Strain

A PHB was produced in the same way as in Reference Example 1 except that instead of the KNK-005 REP-phaJ4b ΔphaZ1::PlacN15SDM-phaC$_{Re}$ ΔphaZ2,6 strain, a *C. necator* H16 strain was used. About the resultant PHB, the average copolymerization proportion of its monomer unit species was measured, and further an annealing method was used to calculate out the presumed content by percentage of its PHA having a melting point of 136 to 155° C., and that of its PHA component having a melting point of 160 to 185° C. The results are shown in Table 1.

TABLE 1

| | Copolymerization proportion (mol %) | | Low-melting-point (90-135° C.) component Tm-Low | Middle-melting-point (136-155° C.) component according to 130° C. annealing method | | High-melting-point (160-185° C.) component according to 160° C. annealing method | |
|---|---|---|---|---|---|---|---|
| | | | | Tm-Mid | Middle-melting-point component | Tm-High | High-melting-point component |
| | 3HB | 3HH | (° C.) | (° C.) | (wt %) | (° C.) | (Wt %) |
| Comparative Example 1 | 89.6 | 10.4 | 108, 126 | — | 0 | — | 0 |
| Comparative Example 2 | 95.0 | 5.0 | — | 136, 145 | 100 | — | 0 |
| Comparative Example 3 | 100 | 0 | — | — | 0 | 172 | 100 |
| Reference Example 1 | 88.3 | 11.7 | 108, 118 | — | 0 | 168 | 0.2 |
| Reference Example 2 | 89.4 | 10.6 | 113 | — | 0 | 166 | 6.8 |
| Example 1 | 89.6 | 10.4 | 111, 125 | 141, 148 | 8.5 | 168 | 0.1 |
| Example 2 | 90.7 | 9.3 | 121, 132 | 144 | 21.6 | 168 | 0.2 |
| Example 3 | 90.1 | 9.9 | 118 | 144 | 2.7 | 167 | 5.5 |

TABLE 2

Crystallization evaluation of produced PHAs

| | Copolymerization proportion (mol %) | | Tc | Hc |
|---|---|---|---|---|
| | 3HB | 3HH | (° C.) | (mJ/mg) |
| Comparative Example 1 | 89.6 | 10.4 | 57 | 27.4 |
| Reference Example 1 | 88.3 | 11.7 | 60 | 33.0 |
| Reference Example 2 | 89.4 | 10.6 | 82 | 32.7 |
| Example 1 | 89.6 | 10.4 | 57 | 34.0 |
| Example 2 | 90.7 | 9.3 | 78 | 39.0 |
| Example 3 | 90.1 | 9.9 | 82 | 33.5 |

Initially about Table 1, according to the results of Reference Examples 1 and 2, in the case of co-expressing the gene encoding the single PHA synthase species derived from *Aeromonas caviae*, and the gene encoding the PHA synthase derived from *Cupriavidus necator*, the following were co-produced: a low-melting-point PHA component having a melting point around 110° C.; and a high-melting-point PHA component having a melting point of 160° C. or higher. However, no middle-melting-point PHA component having a melting point of 136 to 155° C. was produced.

In the meantime, it has been made evident from the results of Examples 1 to 3 that in the case of co-expressing the genes encoding the two PHA synthase species different in substrate specificity from each other and derived from the genus *Aeromonas* (Example 1), or in the case of co-expressing the genes encoding these two PHA synthase species together with the gene encoding the PHA synthase derived from *Cupriavidus necator* (Examples 2 and 3), the low-melting-point PHA component and the high-melting-point PHA component are produced together with the middle-melting-point PHA component.

Evaluation results of PHA crystallization are shown in Table 2. In the case of co-producing the low-melting-point PHA component and the high-melting-point PHA component (Reference Examples 1 and 2), a rise in the Tc and an increase in the Hc were more remarkably recognized than in Comparative Example 1, in which the low-melting-point PHA component was produced. It has been understood from this matter that when the low-melting-point PHA component and the high-melting-point PHA component are co-produced, the PHBH crystallization is made more rapid.

In the meantime, in the case of co-expressing the genes encoding the two PHA synthase species different in substrate specificity from each other and derived from the genus *Aeromonas* (Example 1), three PHBH species different in melting point from each other were produced, and an increase in the Hc was more remarkably recognized than in Comparative Example 1. It has been made evident from this matter that when three PHBH species different in melting point from each other are co-produced, the crystallization of the PHBHs is made more rapid.

Furthermore, in the case of co-expressing the genes encoding the two PHA synthase species different in substrate specificity from each other and derived from the genus *Aeromonas* together with the gene encoding the PHA synthase derived from *Cupriavidus necator* (Examples 2 and 3), an evident rise in the Tc and an evident increase in the Hc were recognized. It has been made evident, particularly, from a comparison between Examples 2 and 3 that even when the content of the high-meting-point PHA component is small in PHAs, the PHAs are made large in crystallization speed when the content of the middle-melting-point PHA component is large therein.

The invention claimed is:

1. A microorganism, comprising genes encoding at least two PHA synthases which are different in substrate specificity toward 3-hydroxyhexanoic acid from each other and are obtained from the genus *Aeromonas*, wherein the microorganism is a transformant of a host, and wherein the host is a microorganism belonging to the genus *Cupriavidus*, and wherein one of the at least two PHA synthases which has a higher substrate specificity toward 3-hydroxyhexanoic acid has an amino acid sequence in which $149^{th}$ asparagine in the amino acid sequence of SEQ ID NO: 1 is substituted with serine, and/or $171^{th}$ aspartic acid in the amino acid sequence of SEQ ID NO: 1 is substituted with glycine.

2. The microorganism according to claim 1, wherein the at least two PHA synthases are capable of synthesizing a copolymer PHA comprising, as its monomer unit species, 3-hydroxybutvric acid and 3-hydroxyhexanoic acid.

3. The microorganism according to claim 1, wherein one of the genes encoding the at least two PHA synthases encodes a PHA synthase which has a lower substrate specificity toward 3-hydroxyhexanoyl-CoA and has the amino acid sequence of SEQ ID NO: 1.

4. The microorganism according to claim 1, wherein one of the genes encoding the at least two PHA synthases encodes a PHA synthase which has a lower substrate specificity toward 3-hydroxyhexanoic acid and has an amino acid sequence in which 505th alanine in the amino acid sequence of SEQ ID NO: 1 is substituted with an amino acid other than alanine.

5. The microorganism according to claim 1, further comprising a gene encoding a PHA synthase which is derived from the genus *Cupriavidus*.

6. The microorganism according to claim 1, wherein the microorganism belonging to the genus *Cupriavidus* is *Cupriavidus necator*.

7. The microorganism according to claim 1, further comprising a gene encoding R-body-specific enoyl-CoA hydratase.

8. The microorganism according to claim 1, wherein one of the at least two PHA synthases that has a lower substrate specificity toward 3-hydroxyhexanoic acid is a PHA synthase comprising the amino acid sequence of SEQ ID NO: 1.

9. A method for producing a PHA mixture, comprising culturing the microorganism of claim 1.

10. The method for producing a PHA mixture according to claim 9, wherein at least one of the at least two PHAs in the PHA mixture comprises, as its monomer unit species, 3-hydroxybutyric acid and 3-hydroxyhexanoic acid.

11. The method for producing a PHA mixture according to claim 9, wherein from the at least two PHAs in the PHA mixture, a PHA having a highest melting point is a PHA having an endothermic peak at 160 to 185° C. in a DSC yielded by annealing the mixture at 160° C.

12. The method for producing a PHA mixture according to claim 9, wherein from the at least two PHAs in the PHA mixture, a PHA having a lowest melting point is a PHA having an endothermic peak at 90 to 135° C. in a DSC of the PHA mixture.

* * * * *

SEQUENCE LISTING

```
<160> NUMBER OF SEQ ID NOS: 32

<210> SEQ ID NO 1
<211> LENGTH: 594
<212> TYPE: PRT
<213> ORGANISM: Aeromonas caviae

<400> SEQUENCE: 1

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu
        35                  40                  45

Gln Gly Ser Gln Gln Pro Trp Gln Leu Ile Gln Ala Gln Met Asn Trp
    50                  55                  60

Trp Gln Asp Gln Leu Lys Leu Met Gln His Thr Leu Leu Lys Ser Ala
65                  70                  75                  80

Gly Gln Pro Ser Glu Pro Val Ile Thr Pro Glu Arg Ser Asp Arg Arg
                85                  90                  95

Phe Lys Ala Glu Ala Trp Ser Glu Gln Pro Ile Tyr Asp Tyr Leu Lys
            100                 105                 110

Gln Ser Tyr Leu Leu Thr Ala Arg His Leu Leu Ala Ser Val Asp Ala
        115                 120                 125

Leu Glu Gly Val Pro Gln Lys Ser Arg Glu Arg Leu Arg Phe Phe Thr
    130                 135                 140

Arg Gln Tyr Val Asn Ala Met Ala Pro Ser Asn Phe Leu Ala Thr Asn
145                 150                 155                 160

Pro Glu Leu Leu Lys Leu Thr Leu Glu Ser Asp Gly Gln Asn Leu Val
                165                 170                 175

Arg Gly Leu Ala Leu Leu Ala Glu Asp Leu Glu Arg Ser Ala Asp Gln
            180                 185                 190

Leu Asn Ile Arg Leu Thr Asp Glu Ser Ala Phe Glu Leu Gly Arg Asp
        195                 200                 205

Leu Ala Leu Thr Pro Gly Arg Val Val Gln Arg Thr Glu Leu Tyr Glu
    210                 215                 220

Leu Ile Gln Tyr Ser Pro Thr Thr Glu Val Gly Lys Thr Pro Val
225                 230                 235                 240
```

```
Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
            260                 265                 270

Phe Met Ile Ser Trp Arg Asn Pro Gly Val Ala Gln Ala Gln Ile Asp
        275                 280                 285

Leu Asp Asp Tyr Val Val Asp Gly Val Ile Ala Ala Leu Asp Gly Val
    290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
            340                 345                 350

Phe Ser Gln Pro Gly Glu Leu Gly Ile Phe Ile His Glu Pro Ile Ile
        355                 360                 365

Ala Ala Leu Glu Ala Gln Asn Glu Ala Lys Gly Ile Met Asp Gly Arg
    370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
            420                 425                 430

His Asn Ser Leu Leu Arg Arg Leu Tyr Leu Glu Asn Gln Leu Val Lys
        435                 440                 445

Gly Glu Leu Lys Ile Arg Asn Thr Arg Ile Asp Leu Gly Lys Val Lys
    450                 455                 460

Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
                485                 490                 495

Leu Leu Ala Glu Ser Gly His Ile Ala Gly Ile Ile Asn Pro Pro Ala
            500                 505                 510

Ala Asn Lys Tyr Gly Phe Trp His Asn Gly Ala Glu Ala Glu Ser Pro
        515                 520                 525

Glu Ser Trp Leu Ala Gly Ala Thr His Gln Gly Gly Ser Trp Trp Pro
    530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
            580                 585                 590

Ala Ala

<210> SEQ ID NO 2
<211> LENGTH: 589
<212> TYPE: PRT
<213> ORGANISM: Cupriavidus necator

<400> SEQUENCE: 2

Met Ala Thr Gly Lys Gly Ala Ala Ala Ser Thr Gln Glu Gly Lys Ser
1               5                   10                  15
```

-continued

```
Gln Pro Phe Lys Val Thr Pro Gly Pro Phe Asp Pro Ala Thr Trp Leu
                20                  25                  30

Glu Trp Ser Arg Gln Trp Gln Gly Thr Glu Gly Asn Gly His Ala Ala
        35                  40                  45

Ala Ser Gly Ile Pro Gly Leu Asp Ala Leu Ala Gly Val Lys Ile Ala
    50                  55                  60

Pro Ala Gln Leu Gly Asp Ile Gln Gln Arg Tyr Met Lys Asp Phe Ser
65                  70                  75                  80

Ala Leu Trp Gln Ala Met Ala Glu Gly Lys Ala Glu Ala Thr Gly Pro
                85                  90                  95

Leu His Asp Arg Arg Phe Ala Gly Asp Ala Trp Arg Thr Asn Leu Pro
            100                 105                 110

Tyr Arg Phe Ala Ala Ala Phe Tyr Leu Leu Asn Ala Arg Ala Leu Thr
        115                 120                 125

Glu Leu Ala Asp Ala Val Glu Ala Asp Ala Lys Thr Arg Gln Arg Ile
    130                 135                 140

Arg Phe Ala Ile Ser Gln Trp Val Asp Ala Met Ser Pro Ala Asn Phe
145                 150                 155                 160

Leu Ala Thr Asn Pro Glu Ala Gln Arg Leu Leu Ile Glu Ser Gly Gly
                165                 170                 175

Glu Ser Leu Arg Ala Gly Val Arg Asn Met Met Glu Asp Leu Thr Arg
            180                 185                 190

Gly Lys Ile Ser Gln Thr Asp Glu Ser Ala Phe Glu Val Gly Arg Asn
        195                 200                 205

Val Ala Val Thr Glu Gly Ala Val Val Phe Glu Asn Glu Tyr Phe Gln
    210                 215                 220

Leu Leu Gln Tyr Lys Pro Leu Thr Asp Lys Val His Ala Arg Pro Leu
225                 230                 235                 240

Leu Met Val Pro Pro Cys Ile Asn Lys Tyr Tyr Ile Leu Asp Leu Gln
                245                 250                 255

Pro Glu Ser Ser Leu Val Arg His Val Val Glu Gln Gly His Thr Val
            260                 265                 270

Phe Leu Val Ser Trp Arg Asn Pro Asp Ala Ser Met Ala Gly Ser Thr
        275                 280                 285

Trp Asp Asp Tyr Ile Glu His Ala Ala Ile Arg Ala Ile Glu Val Ala
    290                 295                 300

Arg Asp Ile Ser Gly Gln Asp Lys Ile Asn Val Leu Gly Phe Cys Val
305                 310                 315                 320

Gly Gly Thr Ile Val Ser Thr Ala Leu Ala Val Leu Ala Ala Arg Gly
                325                 330                 335

Glu His Pro Ala Ala Ser Val Thr Leu Leu Thr Thr Leu Leu Asp Phe
            340                 345                 350

Ala Asp Thr Gly Ile Leu Asp Val Phe Val Asp Glu Gly His Val Gln
        355                 360                 365

Leu Arg Glu Ala Thr Leu Gly Gly Gly Ala Gly Ala Pro Cys Ala Leu
    370                 375                 380

Leu Arg Gly Leu Glu Leu Ala Asn Thr Phe Ser Phe Leu Arg Pro Asn
385                 390                 395                 400

Asp Leu Val Trp Asn Tyr Val Val Asp Asn Tyr Leu Lys Gly Asn Thr
                405                 410                 415

Pro Val Pro Phe Asp Leu Leu Phe Trp Asn Gly Asp Ala Thr Asn Leu
            420                 425                 430

Pro Gly Pro Trp Tyr Cys Trp Tyr Leu Arg His Thr Tyr Leu Gln Asn
```

|  |  |  | 435 |  |  |  | 440 |  |  |  | 445 |  |
|--|--|--|--|--|--|--|--|--|--|--|--|--|

Glu Leu Lys Val Pro Gly Lys Leu Thr Val Cys Gly Val Pro Val Asp
    450                        455                  460

Leu Ala Ser Ile Asp Val Pro Thr Tyr Ile Tyr Gly Ser Arg Glu Asp
465                  470                    475                  480

His Ile Val Pro Trp Thr Ala Ala Tyr Ala Ser Thr Ala Leu Leu Ala
                485                    490                  495

Asn Lys Leu Arg Phe Val Leu Gly Ala Ser Gly His Ile Ala Gly Val
        500                    505                  510

Ile Asn Pro Pro Ala Lys Asn Lys Arg Ser His Trp Thr Asn Asp Ala
            515                520                525

Leu Pro Glu Ser Pro Gln Gln Trp Leu Ala Gly Ala Ile Glu His His
    530                      535                  540

Gly Ser Trp Trp Pro Asp Trp Thr Ala Trp Leu Ala Gly Gln Ala Gly
545                  550                    555                  560

Ala Lys Arg Ala Ala Pro Ala Asn Tyr Gly Asn Ala Arg Tyr Arg Ala
                565                    570                  575

Ile Glu Pro Ala Pro Gly Arg Tyr Val Lys Ala Lys Ala
        580                    585

<210> SEQ ID NO 3
<211> LENGTH: 842
<212> TYPE: DNA
<213> ORGANISM: Cupriavidus necator

<400> SEQUENCE: 3

```
cccgggcaag taccttgccg acatctatgc gctggcgcgc acgcgcctgg cgcgcgccgg    60
ctgtaccgag gtctacggcg gcgacgcctg caccgtggcc gacgccggtc gcttctactc   120
ctatcggcgc gatggcgtga ccggccgcat ggccagcctg gtctggctgg cggactgagc   180
ccgccgctgc ctcactcgtc cttgcccctg gccgcctgcg cgcgctcggc ttcagccttg   240
cgtcggcggc ggccgggcgt gcccatgatg tagagcacca cgccaccgg cgccatgcca   300
tacatcagga aggtggcaac gcctgccacc acgttgtgct cggtgatcgc catcatcagc   360
gccacgtaga gccagccaat ggccacgatg tacatcaaaa attcatcctt ctcgcctatg   420
ctctggggcc tcggcagatg cgagcgctgc ataccgtccg gtaggtcggg aagcgtgcag   480
tgccgaggcg gattcccgca ttgacagcgc gtgcgttgca aggcaacaat ggactcaaat   540
gtctcggaat cgctgacgat tcccaggttt ctccggcaag catagcgcat ggcgtctcca   600
tgcgagaatg tcgcgcttgc cggataaaag gggagccgct atcggaatgg acgcaagcca   660
cggccgcagc aggtgcggtc gagggcttcc agccagttcc agggcagatg tgccggcaga   720
ccctcccgct ttggggagg cgcaagccgg tccattcgg atagcatctc cccatgcaaa   780
gtgccggcca gggcaatgcc cggagccggt tcgaatagtg acggcagaga gacaatcaaa   840
tc                                                                  842
```

<210> SEQ ID NO 4
<211> LENGTH: 232
<212> TYPE: DNA
<213> ORGANISM: Escherichia coli

<400> SEQUENCE: 4

```
tgcttctggc gtcaggcagc catcggaagc tgtggtatgg ctgtgcaggt cgtaaatcac    60
tgcataattc gtgtcgctca aggcgcactc ccgttctgga taatgttttt tgcgccgaca   120
```

```
tcataacggt tctggcaaat attctgaaat gagctgttga caattaatca tcgaactagt      180
taactagtac gcaagttcac agcggataac aatttcacac aggaaacaat tg             232
```

<210> SEQ ID NO 5
<211> LENGTH: 236
<212> TYPE: DNA
<213> ORGANISM: Artificial Sequence
<220> FEATURE:
<223> OTHER INFORMATION: Artificial promoter sequence

<400> SEQUENCE: 5

```
caattgtgct tctggcgtca ggcagccatc ggaagctgtg gtatggctgt gcaggtcgta       60
aatcactgca taattcgtgt cgctcaaggc gcactcccgt tctggataat gttttttgcg      120
ccgacatcat aacggttctg gcaaatattc tgaaatgagc tgttgacaat taatcatccg      180
gctcgtataa tgtgtggaat tgtgagcgga taacaatttc acaggaaaca caattg          236
```

<210> SEQ ID NO 6
<211> LENGTH: 24
<212> TYPE: DNA
<213> ORGANISM: Cupriavidus necator

<400> SEQUENCE: 6

```
cacgtgcaga gagacaatca aatc                                             24
```

<210> SEQ ID NO 7
<211> LENGTH: 34
<212> TYPE: DNA
<213> ORGANISM: Artificial Sequence
<220> FEATURE:
<223> OTHER INFORMATION: primer

<400> SEQUENCE: 7

```
gcgcgcattt aaatgcaagc agttcggcgt ggcg                                  34
```

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8

```
gcttgctctt cctattcagt caggg                                            25
```

<210> SEQ ID NO 9
<211> LENGTH: 43
<212> TYPE: DNA
<213> ORGANISM: Artificial Sequence
<220> FEATURE:
<223> OTHER INFORMATION: primer

<400> SEQUENCE: 9

```
gcagagagac aatcaaatca tgaagaccta cgagaacatc gcc                        43
```

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10

```
gcgcgcattt aaattcaggg aaagcgccgc agg                                   33
```

<210> SEQ ID NO 11
<211> LENGTH: 45
<212> TYPE: DNA
<213> ORGANISM: Artificial Sequence
<220> FEATURE:
<223> OTHER INFORMATION: primer

<400> SEQUENCE: 11
ccctgactga ataggaagag caagccccgg gcaagtacct tgccg    45

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
catgatttga ttgtctctct gc    22

<210> SEQ ID NO 13
<211> LENGTH: 1785
<212> TYPE: DNA
<213> ORGANISM: Artificial Sequence
<220> FEATURE:
<223> OTHER INFORMATION: Artificially mutated gene encoding PHA synthase
      derived from Aeromonas caviae

<400> SEQUENCE: 13

| | |
|---|---|
| atgagccaac catcttatgg cccgctgttc gaggccctgg cccactacaa tgacaagctg | 60 |
| ctggccatgg ccaaggccca gacagagcgc accgcccagg cgctgctgca gaccaatctg | 120 |
| gacgatctgg gccaggtgct ggagcagggc agccagcaac cctggcagct gatccaggcc | 180 |
| cagatgaact ggtggcagga tcagctcaag ctgatgcagc acaccctgct caaaagcgca | 240 |
| ggccagccga cgagccggt gatcaccccg gagcgcagcg atcgccgctt caaggccgag | 300 |
| gcctggagcg aacaacccat ctatgactac ctcaagcagt cctacctgct caccgccagg | 360 |
| cacctgctgg cctcggtgga tgccctggag gcgtccccc agaagagccg ggagcggctg | 420 |
| cgtttcttca cccgccagta cgtcagcgcc atggccccca gcaacttcct ggccaccaac | 480 |
| cccgagctgc tcaagctgac cctggagtcc ggcggccaga acctggtgcg cggactggcc | 540 |
| ctcttggccg aggatctgga gcgcagcgcc gatcagctca catccgcct gaccgacgaa | 600 |
| tccgccttcg agctcgggcg ggatctggcc ctgacccccg gccgggtggt gcagcgcacc | 660 |
| gagctctatg agctcattca gtacagcccg actaccgaga cggtgggcaa gacacctgtg | 720 |
| ctgatagtgc cgccccttcat caacaagtac tacatcatgg acatgcggcc cagaactcc | 780 |
| ctggtcgcct ggctggtcgc ccagggccag acggtattca tgatctcctg gcgcaacccg | 840 |
| ggcgtggccc aggcccaaat cgatctcgac gactacgtgg tggatggcgt catcgccgcc | 900 |
| ctggacggcg tggaggcggc caccggcgag cgggaggtgc acggcatcgg ctactgcatc | 960 |
| ggcggcaccg ccctgtcgct cgccatgggc tggctggcgg cgcggcgcca gaagcagcgg | 1020 |
| gtgcgcaccg ccaccctgtt cactaccctg ctggacttct cccagcccgg ggagcttggc | 1080 |
| atcttcatcc acgagcccat catagcggcg ctcgaggcgc aaaatgaggc caagggcatc | 1140 |
| atggacgggc gccagctggc ggtctccttc agcctgctgc gggagaacag cctgtactgg | 1200 |
| aactactaca tcgacagcta cctcaagggt cagagcccgg tggccttcga tctgctgcac | 1260 |
| tggaacagcg acagcaccaa tgtggcgggc aagacccaca cagcctgct gcgccgtctc | 1320 |

```
tacctggaga accagctggt gaaggggggag ctcaagatcc gcaacacccg catcgatctc    1380
ggcaaggtga agaccccctgt gctgctggtg tcggcggtgg acgatcacat cgccctctgg    1440
cagggcacct ggcagggcat gaagctgttt ggcgggagc agcgcttcct cctggcggag     1500
tccggccaca tcgccggcat catcaacccg ccggccgcca acaagtacgg cttctggcac    1560
aacggggccg aggccgagag cccggagagc tggctggcag gggcgacgca ccagggcggc    1620
tcctggtggc ccgagatgat gggctttatc cagaaccgtg acgaagggtc agagcccgtc    1680
cccgcgcggg tcccggagga agggctggcc ccgcccccg gccactatgt caaggtgcgg     1740
ctcaaccccg tgtttgcctg cccaacagag gaggacgccg catga                    1785
```

```
<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
gcgcgcattt aaatcatggc atctacgccg tcgg                                 34

<210> SEQ ID NO 15
<211> LENGTH: 38
<212> TYPE: DNA
<213> ORGANISM: Artificial Sequence
<220> FEATURE:
<223> OTHER INFORMATION: primer

<400> SEQUENCE: 15
actagtatcg atcaattggc cttttctgcc tgggtcta                             38

<210> SEQ ID NO 16
<211> LENGTH: 38
<212> TYPE: DNA
<213> ORGANISM: Artificial Sequence
<220> FEATURE:
<223> OTHER INFORMATION: primer

<400> SEQUENCE: 16
caattgatcg atactagtat tgcgggcgtt tcttcttg                             38

<210> SEQ ID NO 17
<211> LENGTH: 34
<212> TYPE: DNA
<213> ORGANISM: Artificial Sequence
<220> FEATURE:
<223> OTHER INFORMATION: primer

<400> SEQUENCE: 17
gcgcgcattt aaatacgctg gcgcgtttcg tctg                                 34

<210> SEQ ID NO 18
<211> LENGTH: 18
<212> TYPE: DNA
<213> ORGANISM: Artificial Sequence
<220> FEATURE:
<223> OTHER INFORMATION: linker sequence

<400> SEQUENCE: 18
caattgatcg atactagt                                                   18

<210> SEQ ID NO 19
```

```
<211> LENGTH: 44
<212> TYPE: DNA
<213> ORGANISM: Artificial Sequence
<220> FEATURE:
<223> OTHER INFORMATION: primer

<400> SEQUENCE: 19
ggcccaattg cacgtgctct ctctcaatca aatcatggcg accg                    44

<210> SEQ ID NO 20
<211> LENGTH: 70
<212> TYPE: DNA
<213> ORGANISM: Artificial Sequence
<220> FEATURE:
<223> OTHER INFORMATION: primer

<400> SEQUENCE: 20
gcgcgcacta gtcggctgcc gactggttga accaggccgg caggtcaggc tcatgccttg   60
gctttgacgt                                                          70

<210> SEQ ID NO 21
<211> LENGTH: 24
<212> TYPE: DNA
<213> ORGANISM: Artificial Sequence
<220> FEATURE:
<223> OTHER INFORMATION: Artificially mutated Shine Dalgarno sequence
      derived from Cupriavidus necator

<400> SEQUENCE: 21
cacgtgctct ctctcaatca aatc                                          24

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gtgcaattgg cgcaacgcaa                                               20

<210> SEQ ID NO 23
<211> LENGTH: 40
<212> TYPE: DNA
<213> ORGANISM: Artificial Sequence
<220> FEATURE:
<223> OTHER INFORMATION: primer

<400> SEQUENCE: 23
aacatacgag ccggaagcat gtgtaaagcc tggggtgcct                         40

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
atgcttccgg ctcgtatgtt g                                             21

<210> SEQ ID NO 25
<211> LENGTH: 23
<212> TYPE: DNA
<213> ORGANISM: Artificial Sequence
<220> FEATURE:
```

<223> OTHER INFORMATION: primer

<400> SEQUENCE: 25
gggcaattgt ttcctgtgtg aaa                                            23

<210> SEQ ID NO 26
<211> LENGTH: 36
<212> TYPE: DNA
<213> ORGANISM: Artificial Sequence
<220> FEATURE:
<223> OTHER INFORMATION: primer

<400> SEQUENCE: 26
gcgcgccaat tgcacgtgca gagagacaat caaatc                              36

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
gcggaattcg cgcaacgcaa ttaatgtgag                                     30

<210> SEQ ID NO 28
<211> LENGTH: 32
<212> TYPE: DNA
<213> ORGANISM: Artificial Sequence
<220> FEATURE:
<223> OTHER INFORMATION: primer

<400> SEQUENCE: 28
gcgcgcgaat tccccgggca agtaccttgc cg                                  32

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
catgatttga ttgtctctct g                                              21

<210> SEQ ID NO 30
<211> LENGTH: 38
<212> TYPE: DNA
<213> ORGANISM: Artificial Sequence
<220> FEATURE:
<223> OTHER INFORMATION: primer

<400> SEQUENCE: 30
cagagagaca atcaaatcat gagccaacca tcttatgg                            38

<210> SEQ ID NO 31
<211> LENGTH: 70
<212> TYPE: DNA
<213> ORGANISM: Artificial Sequence
<220> FEATURE:
<223> OTHER INFORMATION: primer

<400> SEQUENCE: 31
gcgcgcacta gtcggctgcc gactggttga accaggccgg caggtcaggc tcatgcggcg    60
tcctcctctg                                                           70

```
<210> SEQ ID NO 32
<211> LENGTH: 126
<212> TYPE: DNA
<213> ORGANISM: Artificial Sequence
<220> FEATURE:
<223> OTHER INFORMATION: Artificially mutated promoter derived from
      Escherichia coli

<400> SEQUENCE: 32
caattggcgc aacgcaatta atgtgagtta gctcactcat taggcacccc aggctttaca      60
catgcttccg gctcgtatgt tgtgtggaat tgtgagcgga taacaatttc acacaggaaa    120
caattg                                                               126
```